US007025058B2

(12) United States Patent
Armstrong et al.

(10) Patent No.: US 7,025,058 B2
(45) Date of Patent: Apr. 11, 2006

(54) METERED DOSE DELIVERY DEVICE FOR LIQUID AND POWDER AGENTS

(75) Inventors: John C. Armstrong, South Dartmouth, MA (US); Richard C. J. Palson, Medfield, MA (US)

(73) Assignee: New England Pharmaceuticals, Inc., Medfield, MA (US)

( * ) Notice: Subject to any disclaimer, the term of this patent is extended or adjusted under 35 U.S.C. 154(b) by 478 days.

(21) Appl. No.: 10/134,041

(22) Filed: Apr. 26, 2002

(65) Prior Publication Data

US 2003/0015191 A1 Jan. 23, 2003

Related U.S. Application Data

(60) Provisional application No. 60/286,634, filed on Apr. 26, 2001.

(51) Int. Cl.
*A61M 15/00* (2006.01)
*A61M 16/00* (2006.01)
*A61M 15/08* (2006.01)

(52) U.S. Cl. .......................... 128/203.21; 128/203.13; 128/203.15

(58) Field of Classification Search ........... 128/200.22, 128/203.12, 203.15, 203.21
See application file for complete search history.

(56) References Cited

U.S. PATENT DOCUMENTS 3,425,414 A 2/1969 Roche
3,625,403 A 12/1971 Rousselot
3,653,380 A 4/1972 Hansen
3,809,084 A 5/1974 Hansen
3,809,294 A 5/1974 Torgeson
3,888,252 A 6/1975 Side et al.
3,921,637 A 11/1975 Bennie et al.
3,948,264 A 4/1976 Wilke et al.
3,949,751 A 4/1976 Birch et al.
3,998,226 A 12/1976 Harris
4,114,615 A 9/1978 Wetterlin
4,137,914 A 2/1979 Wetterlin
4,500,480 A 2/1985 Cambio, Jr.
4,524,769 A 6/1985 Wetterlin
4,598,704 A 7/1986 Bordoni et al.
4,635,651 A 1/1987 Jacobs
4,674,491 A 6/1987 Brugger et al.
4,693,675 A 9/1987 Venus, Jr.
5,031,610 A 7/1991 Armstrong et al.
5,115,803 A 5/1992 Sioutas
5,119,806 A 6/1992 Palson et al.
5,133,458 A 7/1992 Miller (Continued)

FOREIGN PATENT DOCUMENTS

BE 821152 3/1974

(Continued)

*Primary Examiner*—Glenn Dawson
*Assistant Examiner*—Michael G. Mendoza
(74) *Attorney, Agent, or Firm*—Linda M. Buckley; Lisa S. Hazzard; Edwards & Angell LLP

(57) ABSTRACT

A delivery device for the delivery of an agent to the mouth, nose or other bodily site of a user. The delivery device includes an aerosol canister that is actuated to expel propellant, which captures and disperses the agent. In a preferred embodiment, the propellant captures and disperses the agent into the mouth or nose of a user, and inhalation by the user directs the agent to the lungs of the user. The delivery device is particularly suitable for the treatment of bronchial asthma, respiratory conditions and for the delivery of systemically absorbed agents.

46 Claims, 18 Drawing Sheets

U.S. PATENT DOCUMENTS

| | | | | |
|---|---|---|---|---|
| 5,186,164 | A | 2/1993 | Raghuprasad | |
| 5,267,555 | A | 12/1993 | Pajalich | |
| 5,287,850 | A | 2/1994 | Haber et al. | |
| 5,318,015 | A | 6/1994 | Mansson et al. | |
| 5,337,740 | A | 8/1994 | Armstrong et al. | |
| 5,372,128 | A | 12/1994 | Haber et al. | |
| 5,411,175 | A | 5/1995 | Armstrong et al. | |
| 5,415,162 | A | 5/1995 | Casper et al. | |
| 5,429,122 | A | 7/1995 | Zanen et al. | |
| 5,529,059 | A * | 6/1996 | Armstrong et al. | 128/203.12 |
| 5,562,918 | A * | 10/1996 | Stimpson | 424/451 |
| 5,619,984 | A | 4/1997 | Hodson et al. | |
| 5,669,378 | A | 9/1997 | Pera et al. | |
| 5,715,810 | A | 2/1998 | Palson et al. | |
| 5,740,794 | A | 4/1998 | Smith et al. | |
| 5,743,250 | A | 4/1998 | Gonda et al. | |
| 5,743,251 | A | 4/1998 | Howell et al. | |
| 5,755,221 | A | 5/1998 | Bisgaard | |
| 5,785,049 | A | 7/1998 | Smith et al. | |
| 5,810,004 | A | 9/1998 | Ohki et al. | |
| 5,855,202 | A | 1/1999 | Andrade | |
| 5,875,776 | A | 3/1999 | Vaghefi | |
| 5,921,236 | A | 7/1999 | Ohki et al. | |
| 5,980,867 | A | 11/1999 | Tzou et al. | |
| 6,013,050 | A | 1/2000 | Bellhouse et al. | |
| 6,029,662 | A | 2/2000 | Marcon | |
| 6,039,932 | A | 3/2000 | Govind et al. | |
| 6,045,534 | A | 4/2000 | Jacobsen et al. | |
| 6,054,488 | A | 4/2000 | Oliver et al. | |
| 6,055,979 | A | 5/2000 | Fuchs | |
| 6,089,228 | A | 7/2000 | Smith et al. | |
| 6,126,919 | A | 10/2000 | Stefely et al. | |
| 6,186,141 | B1 * | 2/2001 | Pike et al. | 128/203.12 |
| 6,679,256 | B1 * | 1/2004 | Ingle et al. | 128/203.21 |

FOREIGN PATENT DOCUMENTS

| | | | |
|---|---|---|---|
| BE | 905189 | A | 10/1985 |
| DE | 2704574 | | 2/1976 |
| DE | 3016127 | | 4/1979 |
| DE | 3345722 | A | 12/1983 |
| DE | 19502725 | A1 | 8/1996 |
| DE | 19704849 | A1 | 2/1997 |
| DE | 19533979 | A1 | 3/1997 |
| DE | 19727687 | A1 | 6/1997 |
| DE | 19961300 | A1 | 12/1999 |
| EP | 5585 | | 5/1978 |
| EP | 41783 | | 6/1980 |
| EP | 166476 | A | 5/1984 |
| EP | 303844 | A | 8/1987 |
| EP | 385156 | A | 2/1989 |
| EP | 388621 | A | 2/1989 |
| EP | 406893 | A | 7/1989 |
| EP | 467172 | A | 7/1990 |
| EP | 491426 | A | 12/1990 |
| EP | 525720 | A1 | 8/1991 |
| EP | 528764 | A1 | 8/1991 |
| EP | 696458 | A2 | 8/1994 |
| EP | 1080743 | A1 | 9/1999 |
| EP | 1082971 | A2 | 9/1999 |
| FR | 2276-840 | | 7/1974 |
| FR | 2352556 | | 5/1976 |
| FR | 2667790 | A1 | 4/1991 |
| GB | 2270293 | A | 9/1992 |
| GB | 2340758 | A | 8/1998 |
| JP | 09047509 | A | 5/1995 |
| JP | 09322938 | A | 6/1996 |
| JP | 8-206209 | | 8/1996 |
| JP | 8-206210 | | 8/1996 |
| JP | 8-317977 | | 12/1996 |
| JP | 11-290455 | | 10/1999 |
| NZ | 328156 | A | 4/1997 |
| SU | 2008937 | C1 | 9/1990 |
| WO | WO 89/07464 | A | 2/1988 |
| WO | WO 90/13327 | A | 1/1990 |
| WO | WO 92/05823 | A | 10/1990 |
| WO | WO 92/03175 | A | 11/1990 |
| WO | WO 91/19524 | A | 3/1991 |
| WO | WO 91/06333 | | 5/1991 |
| WO | WO 93/00952 | A1 | 7/1991 |
| WO | WO 93/03784 | A1 | 8/1991 |
| WO | WO 94/08552 | A2 | 10/1992 |
| WO | WO 94/14491 | A1 | 12/1992 |
| WO | WO 93/11818 | | 6/1993 |
| WO | WO 95/16483 | A1 | 5/1994 |
| WO | WO 95/31238 | A1 | 5/1994 |
| WO | WO 96/13290 | A1 | 10/1994 |
| WO | WO 96/28206 | A1 | 3/1995 |
| WO | WO 96/32978 | A1 | 4/1995 |
| WO | WO 98/30263 | A1 | 1/1997 |
| WO | WO 99/30833 | A1 | 11/1998 |
| WO | WO 20/66205 | | 4/1999 |

* cited by examiner

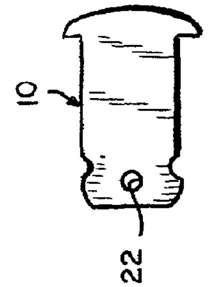
FIG. 12B
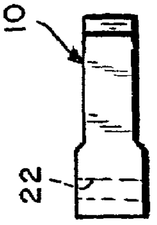
FIG. 12C
FIG. 12A
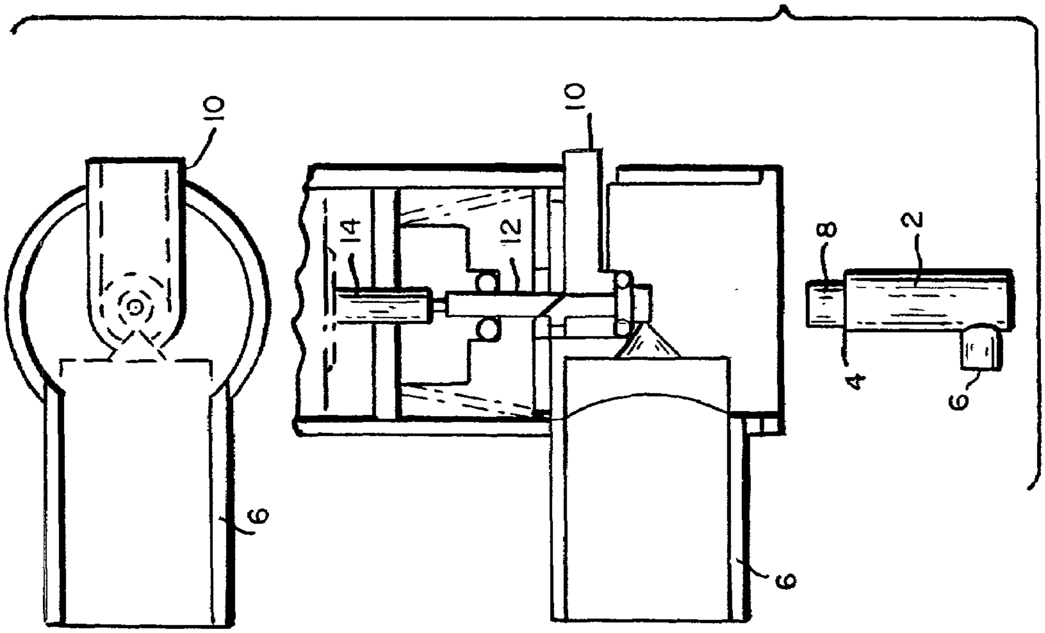

METERED DOSE DELIVERY DEVICE FOR LIQUID AND POWDER AGENTS

The present application claims the benefit of U.S. provisional application No. 60/286,634, filed on Apr. 26, 2001, the teachings of which are incorporated herein by reference.

FIELD OF THE INVENTION

The present invention relates to improved devices for the oral, nasal or topical delivery of finely divided materials, such as medicinal agents and drugs. More particularly, the present invention relates to a device that delivers medicament to the mouth or nose of a user by use of an aerosol canister housing a propellant.

BACKGROUND OF THE INVENTION

Certain disease of the respiratory tract are known to respond to treatment by the direct application of medicinal agents. As many such agents are most readily available as a finely divided material, e.g., in dry powdered form, their delivery is most conveniently accomplished by inhaling the finely divided material through the nose or mouth. This results in better utilization of the medicinal agent in that it is deposited exactly at the site desired and where its action may be required; hence, very minute doses of the therapeutic agent are often equally as efficacious as larger doses administered by other means, with a consequent marked reduction in the incidence of undesired side effects. Alternately, the therapeutic agent in this form may be used for treatment of diseases other than those of the respiratory system, for example, for the delivery of systemically absorbed medicaments such as insulin. When the drug is deposited on the very large surface areas of the respiratory tract, it may be very rapidly absorbed into the blood stream; hence, this method of application may take the place of administration by injection, tablet, or other conventional means.

A variety of inhalation devices for the delivery of finely divided materials are known in the art. For example, U.S. Pat. No. 4,240,418 discloses inhalation devices wherein a container of finely divided material is positioned so that the material from the container can pass by gravity to a delivery area of the device from which it is dispensed. Accordingly, these devices suffer the disadvantage that the use must maintain the device in a particular position so that the finely divided material can pass by gravity to the collecting plate and is not dislodged therefrom prior to dispensing. It appears that such devices also require a large dispensing passage to prevent interference with the free fall of a relatively large load of the finely divided material.

Other known inhalation devices incorporate a deflector (U.S. Pat. No. 4,098,273) or a hollow tube (U.S. Pat. No. 3,938,516) to divert air flow into a chamber to dislodge the finely divided material, thereby requiring a substantial flow of air to disperse the finely divided material. Inhalation sufficient to create such a substantial flow of air is difficult for some users, e.g., asthmatics. Furthermore, it is believed that such devices deliver somewhat imprecise doses due to the inevitable variations in residue of finely divided material left behind in the container after dispensing.

Some known inhalation devices use members which vibrate to dispense the finely divided material, thus increasing the complexity and bulk of the device. For example, the devices of U.S. Pat. No. 3,948,264, utilize batteries to activate vibrators. Other devices incorporate breath activated vibratable members to disperse the finely divided materials. See, e.g., U.S. Pat. Nos. 3,888,253 and 4,995,385 which include a member which vibrates in the airflow to dispense the finely divided material. Still other known devices use a breath activated propeller device to spin the container of finely divided material, thereby casting the material out by centrifugal force, e.g., U.S. Pat. No. 3,507,277. A relatively high velocity of air flow is required to activate such devices, again a problem for breath impaired users.

Moisture in most powders tends to cause agglomeration and clumping thereby inhibiting the breakup and dispersion of the finely divided medication, an essential step in effective dispensing of the material.

However, the manner in which many known devices operate renders hermetic sealing of the container of finely divided material impossible. In still other known devices, the containers for finely divided materials are gelatin capsules which are susceptible to atmospheric moisture.

Recently, inhalation devices have been developed which include an aerosol container housing a mixture of a propellant and a drug. See, e.g., U.S. Pat. Nos. 6,126,919, 6,120,752 and 6,054,488. Certain drugs cannot be successfully mixed with propellants. Further, such mixtures often result in agglomeration of the drug, degradation of the components, chemical instability, and limited shelf lives. In an attempt to solve these problems, certain additives such as, for example, cosolvents, surfactants and dispersants are often added. As a result, pure medicinal agent is not delivered. Further, with such devices, prior to each use, it is required to shake the device vigorously to ensure that the mixture of drug, cosolvents, surfactants, dispersants and other components are suspended in the propellant and to try to provide a uniform mixture of the components. Further, with such devices, it is important to keep track of how much medicine has been used so that the user replaces the device before running out of the medicine. One way this is done is for the user to write a refill date on the device. To figure out the refill date, a user must divide the number of puffs in the device (often, this number is printed the device) by the number of puffs the user takes each day. The resulting number is the number of days the device should last. The user than counts forward that many days to estimate the refill date. However, this process is inconvenient and is often inaccurate because it does not take into account days in which more or fewer puffs are taken.

New and more potent drugs which can be used in increasingly small quantities are being developed on an ongoing basis. In most instances, known inhalation devices for finely divided materials are not capable of delivering such small quantities without the addition of a significant amount of filler. It is highly desirable to minimize the use of such fillers, e.g., in order to reduce the likelihood of side effects.

It can be seen that presently known devices for the delivery of finely divided materials suffer disadvantages which include, among others, imprecise delivery, inability to deliver directly from a hermetically sealed container, agglomeration and clumping of the medicinal agents, reduced shelf life of the medicinal agents, chemical instability, inability to deliver small doses of pure medicinal agent, requirement of good coordination for use and high breath demands upon the user, requirement to shake the device to prevent settling of the medicinal agent, limited portability due to bulk, difficulty to keep track of how much medicinal agent has been used and how much remains and complexity of design. Thus, alternative inhalation devices are being sought.

SUMMARY OF THE INVENTION

The present invention provides a novel device for the oral or nasal delivery of agents, such as medicinal agents and drugs, which reduces or overcomes many deficiencies of prior art devices. More particularly, the present invention relates to a device that delivers an agent to the mouth or nose of a user by means of an aerosol canister housing a propellant. In particular, the present invention provides a device in which the agent and the propellant are kept separated, e.g. in separate containers or compartments, and combined at the instant of actuation. The delivery device may also provide beneficial effects for the delivery of agents to other bodily sites including, for example, the eye and ear.

As used herein, a propellant includes both compressed and liquefied gases. In some embodiments, however, liquefied gases, which require lower pressures than compressed gasses to be liquefied, are preferable to compressed gases.

In an exemplary embodiment, the delivery device includes a body member having an aerosol canister at a first end and a second end for insertion into a user's mouth or nose. A container, housed within the body member between the aerosol canister and the second end, contains an agent. A mechanism for exposing the agent in the container to the propellant is further included. In a preferred embodiment, the mechanism is a piercing member, such as a needle or a blade, housed within the body member between the aerosol canister and the container. Preferably, the mechanism is movable within the body member and, during use, the mechanism, e.g. piercing member or blade, is lined up with the agent in the container and is moved towards and through the container. The agent is then delivered to the mouth or nose of a user by the propellant, which is expelled by actuation of the aerosol canister. The propellant captures and disperses the agent through the second end and into the mouth or nose of the user. Preferably, the propellant is expelled with a force adequate to cause substantially complete dispersion of the agent, and inhalation by the user directs the agent to the lungs of the user.

In a particularly preferred embodiment, the aerosol canister is movable within the body member and the mechanism is a piercing member in connection with the aerosol canister such that, as the aerosol canister is moved within the body member towards the container, the piercing member, likewise, moves towards and through the container. As the aerosol canister moves towards and through the container, it preferably encounters a stop or similar mechanism that actuates the aerosol canister to expel propellant.

In yet another preferred embodiment, the mechanism is a piercing member in the form of a needle having at least a hollow tip portion that pierces and passes through the container. As the hollow tip portion pierces and passes through the container, the agent is picked up within the hollow portion of the piercing member and is carried towards the second end of the body member. Propellant, expelled from the aerosol canister then forces the agent from the needle, through the second end and into the mouth or nose of a user.

Preferably, the piercing member is designed such that it is substantially hollow along its length. As such, when the piercing member is in line with the aerosol canister, propellant expelled from the aerosol canister passes through the hollow of the piercing member. As the propellant travels through the piercing member, it encounters the agent picked up within the piercing member and disperses the agent out of the piercing member into the mouth or nose of the user.

The hollow needle is not limited in its cross sectional shape and, for example, it may have a circular, oval, square, triangular, or other cross sectional shape. In one preferred embodiment, the needle is designed such that the hollow portion is sized to accommodate and pick up a precise dose of agent. For example, the cross section of the hollow portion may be made larger or smaller to accommodate more or less agent.

Preferably, the hollow needle is sized such that the cross section of the needle is substantially the same as the cross section of the portion of the container housing the agent, so as to minimize any residue of agent in the container.

In another preferred embodiment, the mechanism is a piercing member in the form of a solid needle. In this embodiment, as the needle is moved through the container, it picks up the agent in the container and pushes the agent through the container toward the second end of the body member. The agent is then delivered to the mouth or nose of a user by the propellant, which is expelled by actuation of the aerosol canister. The propellant picks up and disperses the agent out of the second end and into the mouth or nose of the user. Preferably, the propellant is expelled with adequate force to substantially completely disperse the agent, and inhalation by the user directs the agent to the lungs of the user.

The solid needle is not limited in its cross sectional shape and it may have, for example, a circular, oval, square, triangular, or other cross sectional shape. Preferably, the solid needle is sized such that the cross section of the needle is substantially the same as the cross section of the portion of the container housing the agent, so as to minimize any residue of agent in the container.

In embodiments where the solid needle is sized with a cross section substantially the same as the cross section of the portion of the container housing the agent, bypass pathways are preferably included in the device. For example, one or more bypass pathway may be formed around the portion of the container housing the agent such that propellant expelled from the aerosol canister passes through the one or more bypass pathway to the second end of the body member where the propellant captures and disperses the agent into the mouth or nose of the user. The bypass pathways may also be included in other embodiments, for example, where the mechanism is a hollow needle.

In some embodiments of the present invention, the solid or hollow needle may be sized with a cross section smaller than the cross section of the portion of the container housing the agent such that at least a portion of the propellant may be expelled through the portion of the container housing the agent around the needle. In this embodiment, the bypass pathways may also be included to allow for additional pathways through which additional propellant can be expelled. Thus, the propellant may be expelled both through the portion of the container housing the agent (e.g. around the needle and through the hollow needle) and through the bypass pathways.

In another embodiment, the piercing member is in the form of a blade having a cross section less than the cross section of the portion of the container housing the agent. As the blade pierces the container, an opening through the container housing the agent is formed. Propellant is then expelled around the blade and through the opening formed by the blade, thereby forcing the agent out of the container, through the second end and into the mouth or nose of a user. In one embodiment, the agent within the container is sealed at the top and/or bottom of the container by a conventional piercable material such as, for example, a plastic or metal film, to ease piercing of the container and to enable further opening up of the container. Thus, as the propellant is forced around the blade through the opening formed by the blade, the force of the propellant against the piercable material surrounding the opening formed by the blade further opens up the piercable material and assists in driving the agent out of the container. In this case, most if not all of the agent in the container will be expelled.

In this blade embodiment, bypass pathways may also be included to allow for additional pathways through which additional propellant can be expelled. Thus, the propellant may be expelled both through the portion of the container housing the agent around the blade and through the bypass pathways.

Preferably, the delivery device is designed to deliver precise doses of agent. This may be accomplished by, for example, sizing the portion of the container housing the agent so as to accommodate a precise dose of agent. For example, the thickness and/or cross-section of the container or portion of the container holding the agent may be increased or decreased to hold more or less agent. This may also be accomplished by, for example, sizing the hollow portion of the piercing member so as to accommodate a particular dose of agent.

The present invention provides delivery devices and methods of use that greatly reduce and, in some instances, eliminate the problems associated with currently available delivery devices. For example, the present delivery devices and methods of use effectively deliver precise doses of agents, prevent agglomeration and clumping of the medicinal agents, are easy to use, require minimal inhalation by the user and are capable of delivering small amounts of medicaments without the use of fillers.

Still further, contrary to devices that mix the medicinal agent with a propellant in an aerosol canister, the present device does not require the agent to come into contact with the propellant until the point in time that the agent is administered. Thus, the agent may be provided in substantially pure form. As a result, the chemical stability of the agent is not diminished by contact with a propellant and the shelf life of the agents is not diminished in this manner. Further, the device need not be shaken well prior to use to prevent settling of the agent.

In preferred embodiments of the present invention, the agent is provided in containers housing individually sealed doses rather than providing a bulk amount of agent mixed in a propellant. Thus, a user need not keep track of uses of the device to estimate how many doses of the medicinal agent remain in the device as with conventional aerosol delivery devices. A user of the present device merely uses the device and replaces the container housing the agent between each use with single dose containers. Alternatively, with multiple dose containers having a plurality of compartments each housing a single dose, a user merely needs to look at the container to see how many compartments have been pierced to see how many doses have been used and how many doses remain. Thus, the potential for erroneously estimating the number of doses remaining is eliminated and a user can eliminate the danger of carrying a delivery device with no remaining doses or fewer doses than believed.

Other aspects and embodiments of the invention are discussed below.

BRIEF DESCRIPTION OF THE DRAWINGS

FIG. 12*a* shows views of another embodiment of the present invention, wherein the container is elongate and can be slid into and out of a slot in the device, like a drawer.

FIG. 12*b* shows an upper enlarged view of an elongate container in accordance with one embodiment of the present invention.

FIG. 12*c* shows a side enlarged view of an elongate container in accordance with one embodiment of the present invention.

DETAILED DESCRIPTION OF THE INVENTION

Figure 3:
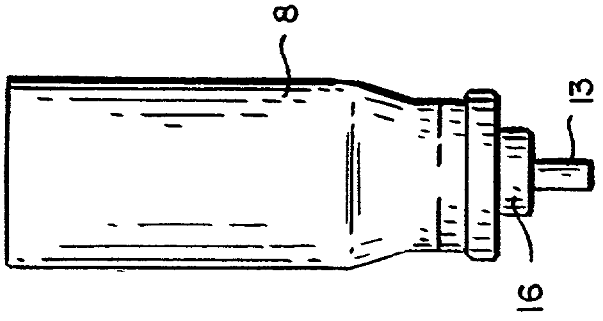
FIG. 3 is a view of the aerosol container within the delivery device of FIG. 1.

Although the delivery devices of the present invention are primarily illustrated and described herein by means of devices which have been adapted for oral delivery, it will be appreciated by those skilled in the art that such devices may also be adapted for nasal and other bodily site delivery. Further, although the devices of the present invention are primarily illustrated and described herein by means of devices having a mechanism in the form of a piercing member, particularly a hollow needle, it will be appreciated by those skilled in the art that such devices may also be adapted having other forms of mechanisms such as solid needles and blades.

Referring now to the various figures of the drawing, wherein like reference characters refer to like parts, there is shown in FIGS. 1–18*e* various views of a delivery device 1, in accordance with the invention.

Figure 1:
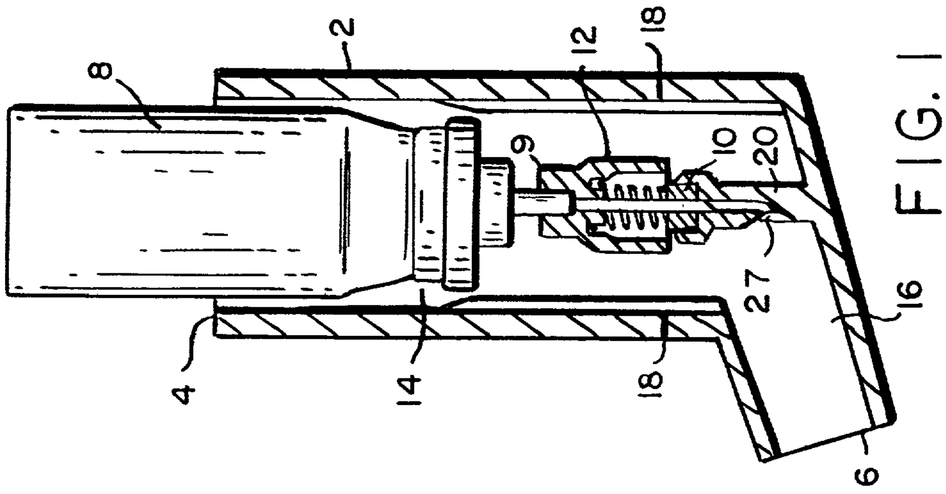
FIG. 1 is a side cross-sectional view of one embodiment of the delivery device in accordance with the present invention.
Figure 6:
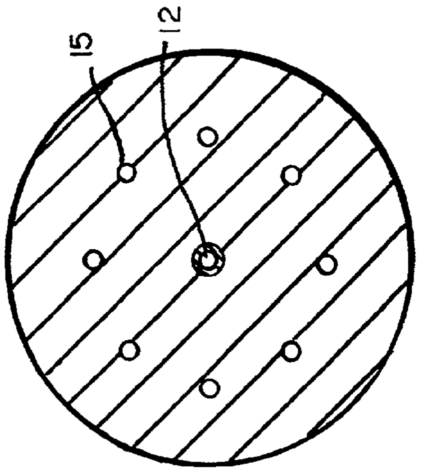
FIG. 6 shows a view of the device shown in FIG. 5 taken along line A—A.

As shown in FIG. 1, the delivery device 1 includes a body member 2 having a first end 4 and a second end 6. An aerosol canister 8, housing a propellant, is located at the first end 4 of the body member 2. The second end 6 is designed for insertion into a user's mouth or nose. A container 10, which contains an agent, is further housed within the body member 2 between the aerosol canister 8 and the second end 6. The delivery device further includes a mechanism for exposing the agent in the container 10 to the propellant. In a preferred embodiment, the mechanism is a piercing member 12, such as a needle or blade, preferably positioned within the body member 2, between the container 10 and the aerosol canister 8. The piercing member 12 is movable within the body member 2 and may be moved so as to pierce and pass through the container 10. The agent within the container 10 is delivered to the mouth or nose of a user by actuation of the aerosol canister 8. Actuation of the aerosol canister 10 expels the propellant from the aerosol canister 10 towards the agent and disperses the agent out of a nozzle 27 into the second end 6 and into the mouth or nose of the user.

The body member 2 may be any convenient shape. As shown in FIG. 1, the body member 2 may be formed of an upper portion 14 and a lower portion 16 extending at an angle from the bottom of the upper portion 14 as is conventional in the art. For example, conventional devices have been formed with an angle between the upper and lower portions ranging from about 110° to about 115°. Such an angled arrangement has been found to assist in directing the propellant and agent to the desired treatment location and makes it easier to comfortably use of the device. Of course, the shape of the body member 2 is not limited to such an arrangement, and other body member 2 shapes may be used.

In a preferred embodiment, the lower portion 16 extends at an angle from the upper portion 14 and is connected to the upper portion 14 via hinges or other fastening means 18 such as, for example, corresponding threaded portions on the upper portion 14 and lower portion 16, that allow the lower portion 16 to be separated from the upper portion 14. Any other type of mechanism that is useful in providing access to the interior of the body member 2 and/or to allow for easy insertion and removal of the container 10 housed within the body member 2 may be used.

Figure 2:
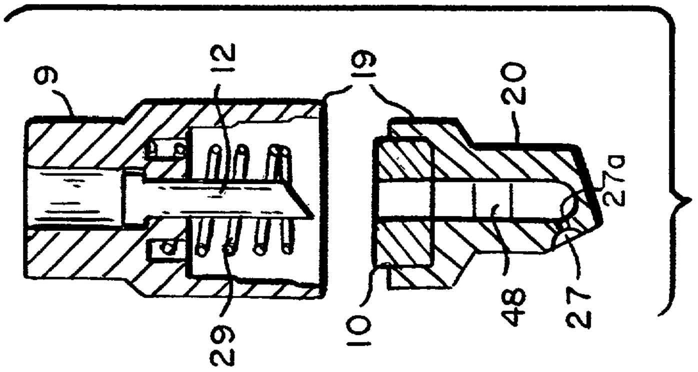
FIG. 2 is an enlarged side cross-sectional view of the piercing member and container portions of the delivery device shown in FIG. 1.

In the embodiment shown in FIGS. 1 and 2, a holding member 20 is mounted within the body member 2 for holding the container 10 in place within the device. For example, the holding member 20 may be mounted in the lower portion 16, as shown in FIG. 1, such that as the lower portion 16 of the body member 2 is separated from the upper portion 14, for example, by swinging the lower portion 16 open along hinges or other fastening means 18, the holding member 20, likewise, swings along with the lower portion 16 and easy access is provided to remove and replace the container 10.

The container 10 may be any convenient shape. In the embodiments shown in FIGS. 6 and 11*a–b*, the container 10 is cylindrical. In the embodiment shown in FIGS. 12*a–c*, the container 10 is elongate. Furthermore, the container 10 may be single or multicompartmental.

Figure 8D:
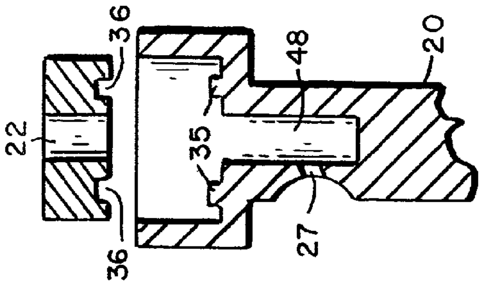
FIG. 8*d* is an enlarged view of a holding member having protrusions and a container having grooves in accordance with one embodiment of the present invention, wherein the grooves in the holding member and protrusions in the container correspond to each other when the container is properly inserted in the holding member.
Figure 8C:
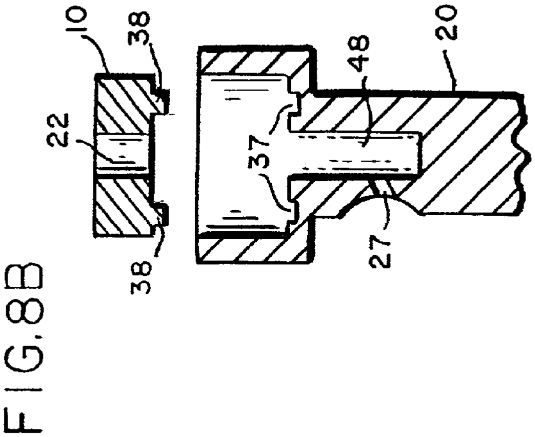
FIG. 8*c* is an enlarged view of a holding member having grooves and a container having protrusions in accordance with one embodiment of the present invention, wherein the grooves in the holding member and protrusions in the container correspond to each other when the container is properly inserted in the holding member.
Figure 8B:
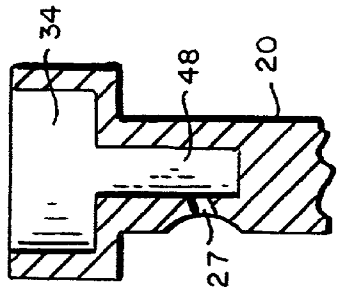
FIG. 8*b* is an enlarged view of a holding member for holding the container of agent in accordance with one embodiment of the present invention.
Figure 8A:
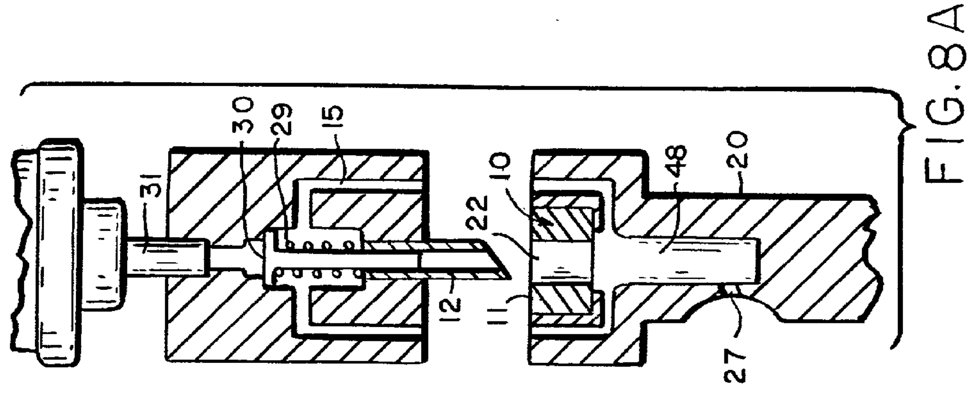
FIG. 8*a* is an enlarged view of the top and bottom portions of the device shown in FIG. 7.

In the embodiment shown in FIG. 1, the holding member 20 is designed to securely hold the container 10 and prevent vertical, horizontal and rotational movement of the container 10 during use. Thus, for example, the holding member 20 may be designed to have an opening 34, as shown in FIG. 8*b*, that is sized and shaped to snugly fit the container 10. In some embodiments, the container 10 has a snap fit within the opening 34 of the holding member 20. In some embodiments, the holding member 20 has an opening 34 that includes one or more protrusions 35 or grooves 37 that correspond to one or more grooves 36 or protrusions 38 in the container 10, so that the container 10 is placed into the opening 34 with the grooves 36 or protrusions 38 of the container 10 engaging the protrusions 35 or grooves 37 in the opening 34 of the holding member 20, as shown, for example, in FIGS. 8*c–d*.

Figure 11A:
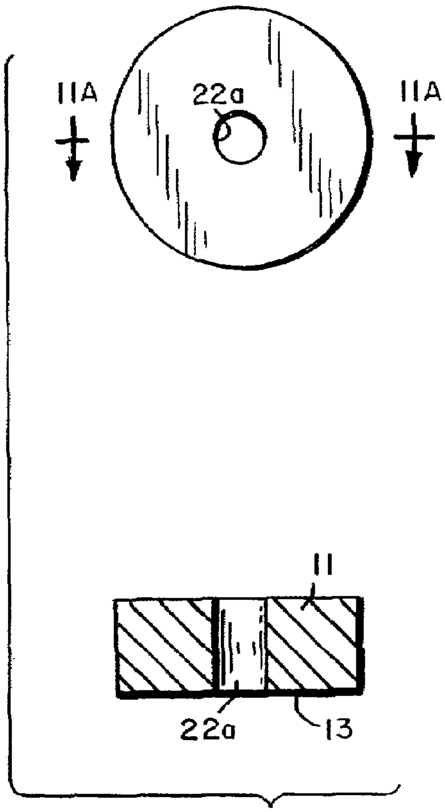
FIG. 11*a* shows an enlarged view of the container having a single center compartment housing the agent.
Figure 11B:
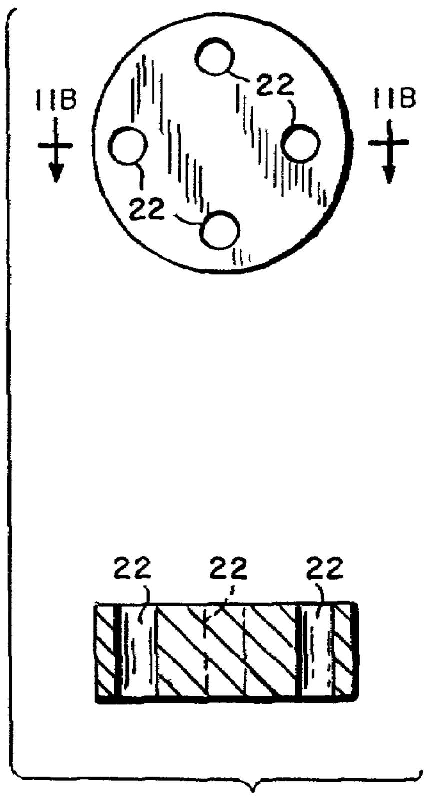
FIG. 11*b* shows an enlarged view of the container having a plurality of compartments housing the agent.

The container 10 and holding member 20 are preferably sized and shaped such that when the container 10 is inserted into the opening 34 of the holding member 20, the container 10 is automatically positioned in line with the aerosol canister 8 and the piercing member 12 or other mechanism. In preferred embodiments, the container 10 is designed such that it is symmetrical left to right and top to bottom, for example, as shown in FIGS. 11*a–b*, so that the container 10 can be quickly and easily inserted into the opening 34 left end first, right end first, facing up or facing down. Alternatively, the container 10 may be designed so that it is, for example, properly inserted facing up, for example, as shown in FIGS. 8*c–d*. To ensure proper insertion, the top end could, for example, be enlarged to a size larger than the opening 10 so that the container 10 could not be inserted facing down because it would not fit. Another way to ensure proper insertion could be to include some type of indicia on the container 10, such as an arrow, indicating the proper direction of insertion.

Figure 13B:
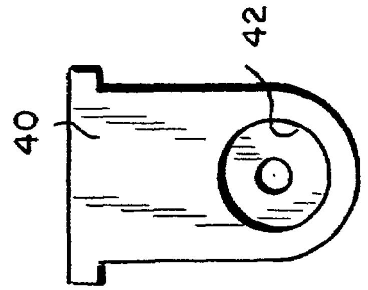
FIG. 13*b* shows an upper enlarged view of a drawer-like holding member in accordance with one embodiment of the present invention.
Figure 13C:
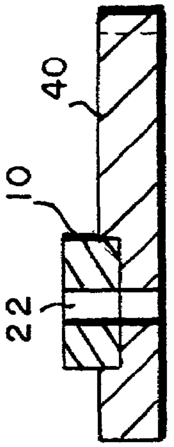
FIG. 13*c* shows a side enlarged view of a drawer-like holding member in accordance with one embodiment of the present invention.
Figure 13A:
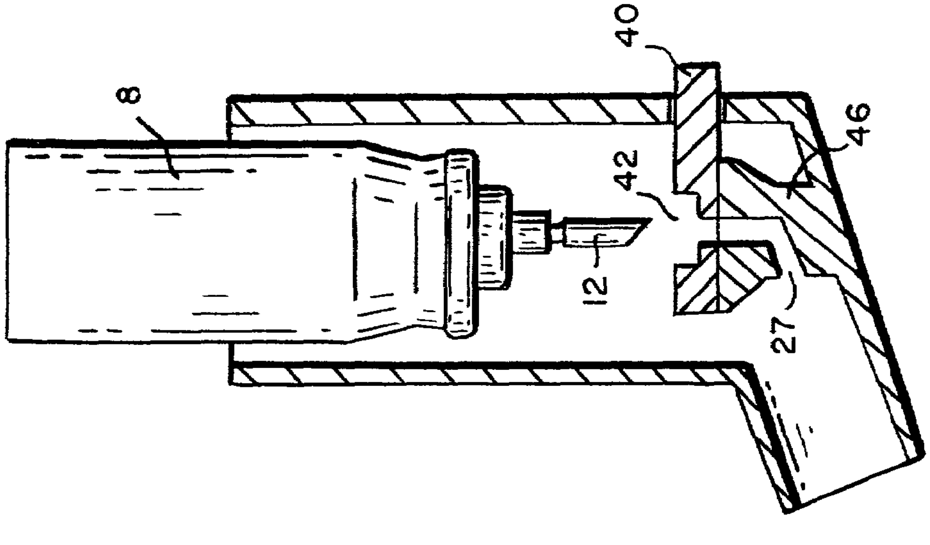
FIG. 13*a* shows a view of another embodiment of the present invention, wherein a drawer-like holding member holds the container of agent and wherein the drawer-like holding member can be slid into and out of a slot in the device.
Figure 14A:
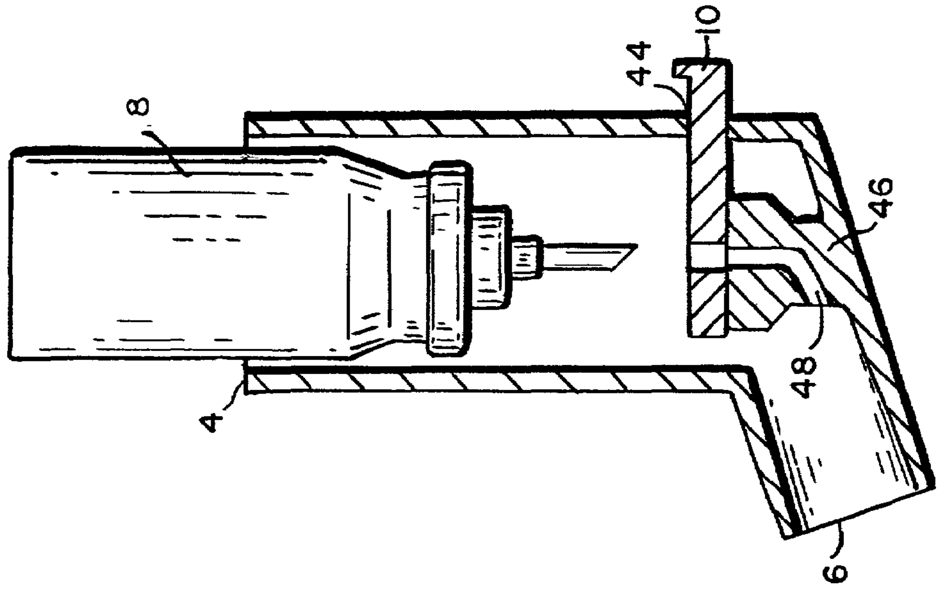
FIG. 14*a* shows a view of another embodiment of the present invention, wherein an elongate container that can be slid into and out of a slot in the device, like a drawer, is stabilized by a vertical stabilizing member.
Figure 14B:
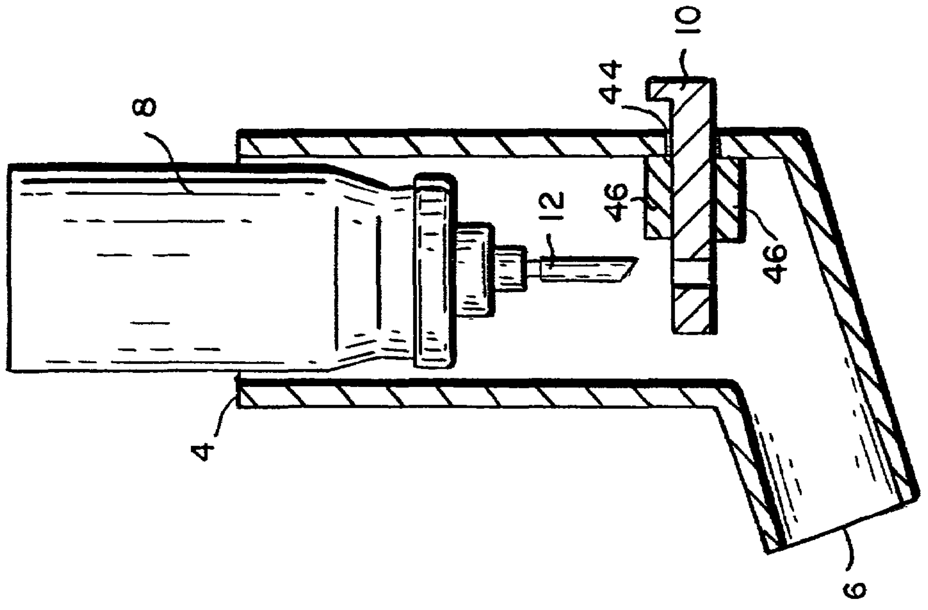
FIG. 14*b* shows a view of another embodiment of the present invention, wherein an elongate container that can be slid into and out of a slot in the device, like a drawer, is stabilized by one or more horizontal stabilizing members.
Figure 15B:
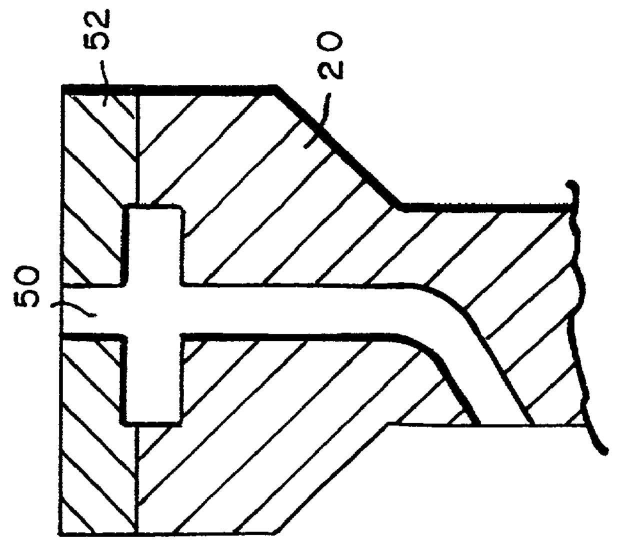
FIG. 15*b* shows FIG. 15*a* without the container or valve stem in place.
Figure 15A:
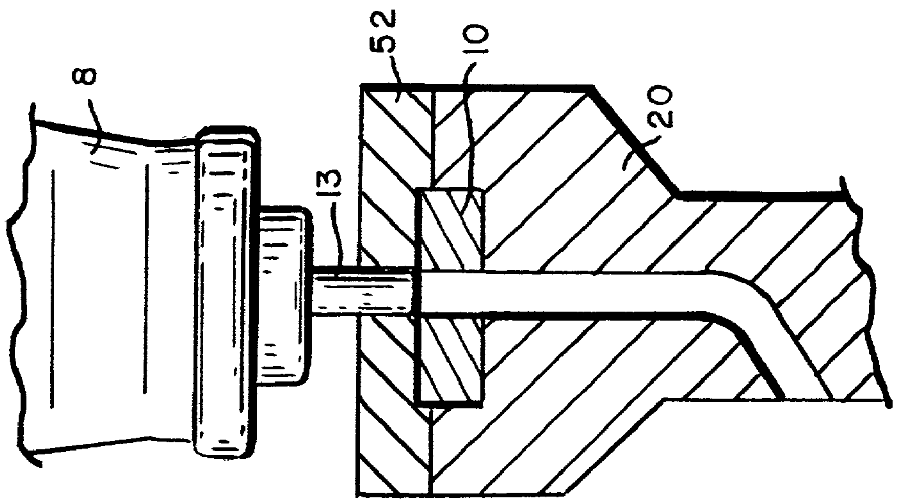
FIG. 15*a* shows an enlarged view of another embodiment of the present invention wherein the mechanism for exposing the agent in the container to the propellant is the valve stem and wherein a stop member or cover is used to form a channel through which the propellant is directed through the container.

In another embodiment, a drawer-like or similar mechanism 40 may be included in the body member 2 such that the drawer-like or similar mechanism may be, for example, pulled out or swung open, thereby providing access to the interior of the body member for insertion and replacement of the container 10. In one preferred embodiment, for example, as shown in FIG. 13, the drawer 40 may be pulled in and out of the body member 2 such that when the drawer 40 is pulled out, the drawer 40 has a bottom surface that is designed as a holding mechanism on which the container 10 is placed and when the drawer 40 is pushed back inside the body member, the container 10 is positioned for use. Preferably, as with the holding member 20, the drawer-like or similar mechanism 40 is designed to securely hold the container 10 and prevent vertical, horizontal and rotational movement of the container 10 during use. Thus, the drawer-like or similar mechanism 40 may, like the holding member, 20 include an opening 42 like that described above for the holding member 20. The container 10 and drawer-like or similar mechanism 40 are preferably sized and shaped such that when the container 10 is inserted into the drawer-like or similar mechanism 40, the container 10 is automatically positioned in line with the aerosol canister 8 and the piercing member 12 or other mechanism. In preferred embodiments, the container 10 is designed such that it is symmetrical left to right and top to bottom so that the container 10 can be quickly and easily inserted into the drawer-like or similar mechanism 40 left end first, right end first, facing up or facing down. Alternatively, the container 10 may be designed so that it is, for example, properly inserted facing up. To ensure proper insertion, the top end could, for example, be enlarged to a size larger than the opening 42 in the drawer-like or similar mechanism 40 so that the container 10 could not be inserted facing down because it would not fit. Another way to ensure proper insertion could be to include some type of indicia on the container 10, such as an arrow, indicating the proper direction of insertion. In some embodiments, one or more stabilizing members 46 are positioned within the body ember 2, for example, as shown in FIGS. 13*a* and 14*b*, on and/or between which the drawer-like or similar mechanism 40 can rest when inserted in the device to prevent the drawer-like or similar mechanism 40 from vertical movement during use. For example, as shown in FIG. 13*a*, a vertically extending stabilizing member 46 is positioned such that the drawer 40, when inserted, rests on the stabilizing member 46 and prevents vertical movement. In another embodiment, as shown in FIG. 14*b*, one or more horizontally extending stabilizing members 46 can be located about the slot 44 such that the drawer 40 or elongate container 10, when inserted rests on or between the one or more horizontally extending stabilizing members 46. These stabilizing members 46 can extend along a portion of the drawer 40 length, for example, as shown in FIG. 14*b* or along the entire drawer 40 length, for example, as shown in FIG. 14*c*. When the stabilizing member(s) 46 extend along the compartment 22 of the container 10 that houses the agent, a lumen 48 is located in the stabilizing member(s) 46 through which the piercing member 12, propellant and agent may pass, for example, as shown in FIG. 14*a*. The horizontally extending stabilizing members 46 prevent the drawer-like or similar mechanism 40 from horizontal movement during use.

In yet another preferred embodiment, rather than provide a drawer-like or similar mechanism 40 for holding the container 10, a slot 44 is located in the body member 2 and the container 10 is designed to slide in and out of the slot 44 much like a drawer. For example, as shown in FIGS. 12*a–c*, the container 10 can be elongate in shape, like a drawer, and the slot 44 is sized and shaped in accordance with the size and shape of the container 10 so that the container 10, when inserted into the slot 44, is held securely and is prevented from vertical, horizontal and rotational movement within the slot 44. The container 10 is preferably sized and shaped such that when it is inserted into the slot 44, it is automatically positioned in line with the aerosol canister 8 and the piercing member 12 or other mechanism. For example, as shown in FIGS. 14*a–b*, the container 10 may be elongate in shape, and inserted into the slot 44 such that at least a portion of one end of the container 10 remains external to the slot or opening for easy removal and replacement. In preferred embodiments, the container 10 is designed such that it is symmetrical left to right and top to bottom so that the container 10 can be quickly and easily inserted left end first, right end first, facing up or facing down. Alternatively, the container 10 may be designed so that it is properly inserted left end first. To ensure proper insertion, the right end could be enlarged to a size larger than the slot or opening so that the container 10 could not be inserted right end first because it would not fit. Another way to ensure proper insertion could be to include some type of indicia on the container 10, such as an arrow, indicating the proper direction of insertion. Further, the container 10 could also be designed such that it is properly inserted facing up. Likewise, the container may be sized to prevent insertion with the container 10 facing down or could include some type of indicia on the container that indicates proper direction of insertion. As with the drawer-like or similar mechanism 40, when the container 10 is in the form of a drawer that is slid into and out of a slot 44, one or more stabilizing members 46 are preferably positioned within the body member 2, for example, as shown in FIG. 14*a–b*, on and/or between which the container 10 can rest when inserted in the device to prevent the container 10 from vertical movement during use. For example, as shown in FIG. 14*a*, a vertically extending stabilizing member 46 is positioned such that the container 10, when inserted, rests on the stabilizing member 46 and prevents vertical movement. In another embodiment, as shown in FIG. 14*b*, one or more horizontally extending stabilizing members 46 can be located about the slot 44 such that the container 10, when inserted rests on or between the one or more horizontally extending stabilizing members 46, which prevent the drawer-like or similar mechanism 40 from horizontal movement during use. These stabilizing members 46 can extend along a portion of the container 10 length, for example, as shown in FIG. 14*b* or along the entire drawer 40 length, for example, as shown in FIGS. 2, 7, 8*a–d*, 13*a*, 14*b* and 15*a–b*. When the stabilizing member(s) 46 extend along the compartment 22 of the container 10 that houses the agent, a lumen 48 is located in the stabilizing member(s) 46 through which the piercing member 12, propellant and agent may pass, for example, as shown in FIG. 14*a*.

The container 10, which houses an agent, is located within the body member 2 between the aerosol canister 8 and the second end 6. The container 10 has a top end 11 and bottom end 13, and the container 10 is housed within the body member 2 such that the piercing member 12 passes through the top end 11 then the bottom end 13 as it pierces and passes through the container 10.

In one embodiment, as best shown in FIGS. 8, 11*a* and 11*b*, the container 10 has one or more compartments 22, 22*a* that house the agent. The one or more compartments 22, 22*a* are depicted as cylindrical in shape. However, the shape of the one or more compartments 22, 22*a* is not particularly limited in shape.

For example, in one embodiment, as shown in FIGS. 8 and 11*a*, the container 10 may be cylindrical in shape and have a singe center compartment 22*a* housing the agent. In this embodiment, the container 10 is positioned within the body member 2 such that the center compartment 22*a* is directly in line with the path of travel of the piercing member 12. However, the portion of the container 10 housing the agent need not be in the center of the container 10 as long as the compartment 22, 22*a* containing the agent is in line with the path of travel of the piercing member 12.

In another embodiment, as shown in FIG. 11*b*, rather than having a single center compartment 22*a* of the container 10 housing the agent, a plurality of compartments 22 within the medicament container 10 may contain the agent such that a single container 10 may contain a plurality of doses of agent. Thus, containers 10 of a given size can contain different numbers of single doses depending upon the requirements of the particular agent in use. Thus, one inhalation device in accordance with the present invention can have many different applications.

The container 10 having a plurality of compartments 22 is preferably mounted within the body member 2 so that the container 10 may be rotated or positioned to line up each of the compartments 22 with the piercing member 12. For example, in one embodiment, the container 10 is disk-like in shape with the plurality of compartments 22 positioned in a circle, see FIG. 11*b*. In this embodiment, the container 10 is preferably rotatably mounted in the body member 2 to allow for a user to line up each compartment 22 with the piercing member 12 by simple rotation of the compartment 10. As such, for example, the container 10 may be rotatably, centrally disposed on a pin or similar mechanism (not shown). The container 10 may further be provided with a conventional locking means (not shown) so that during rotation, the container 10 is locked in position each time a compartment 22 is disposed in line with the path of travel of the piercing member 12, thereby locating each single dose for dispensation. The container 10 can be rotated mechanically or, alternatively, may be rotated by hand. Alternative designs for the medicament container 10 may also be used, such as, for example, multiple compartment strips, either rigid or in flexible rolls, e.g., as in a cartridge belt for an automatic weapon, and so forth. For embodiments wherein the container 10 is in the form of an elongate drawer that is slid into and out of a slot 44 into position, a plurality of compartments 22 can be arranged in a line and the container 10 slid into the slot at varying depths for delivery of agent from each compartment 22. In this embodiment, the container 10 is preferably provided with a conventional locking means (not shown) so that as the container 10 is slid into the slot 44, the container 10 is locked in position each time a compartment 22 is disposed in line with the path of travel of the piercing member 12, thereby locating each single dose for dispensation.

Alternatively, rather than using one or more compartments 22, 22*a* of the container 10 housing the agent, the entire container 10 may be hollow and may house the agent if desired.

The container 10 is typically made of conventional molded plastics, such as acrylic, polypropylene, polyethylene, acetal, ABS and so forth. However, other conventional materials known to those skilled in the art may also be used.

In one embodiment, the portion of the container 10 housing the agent may be sized so as to provide a precise dose of agent to a user. For example, in one embodiment, the agent is housed within one or more compartments 22, 22*a* having a particular diameter and/or height. As the diameter and/or height of the compartment(s) 22, 22*a* increase, more agent may be contained within the compartment(s) 22, 22*a*.

Compartment(s) 22, 22*a* for use in the present invention may be sealed at the top end 11 and bottom end 13 with a conventional piercable material using methods known to those skilled in the art. In such embodiments, the thickness of the piercable material is preferably no greater than about 0.004 inch, more preferably, between about 0.001 and about 0.003 inch, and more preferably, between about 0.001 and about 0.0015 inch. The desired characteristics for such piercable materials are high tensile strength to avoid tearing during perforation and resistance to the passage of moisture. In one preferred embodiment, a polyester film having heat activating adhesive on one side is used to seal the container 10. Although polyester is preferred, other films known in the art, such as aluminum foil, polyolefin and polypropylene may also be employed. In a particularly preferred embodiment, a lamination of aluminum foil and a high tensile strength material, such as a plastic film, is used. For example, the seal may be a multilayered seal fabricated of one or more layers of aluminum foil and one or more layers of polyester, polyolefin and/or polypropylene film. In such embodiments, the aluminum foil layer(s) provide a barrier that protects the agent within the container from moisture and other external elements and the plastic layer(s) provide additional strength to prevent inadvertent piercing of the easily piercable aluminum layer and also assists in preventing the seal from becoming completely detached from the container as the piercing member 12 passes through the seal. For example, in one embodiment, the outermost layer is an aluminum foil layer, followed by an inner polyester layer laminated on the aluminum foil layer. A heat activating adhesive on the polyester layer secures the seal to the container 10. Alternatively, the entire container 10 or the entire top end 11 and bottom end 13 of the container 10 may be fabricated of a piercable material.

In the manufacture of such embodiments, the container 10 is typically first sealed on one side 11 or 13 with the piercable sealing material. The agent is then added to the container 10 and the container 10 is then hermetically sealed by sealing the other side 11 or 13 of the container 10 with the piercable sealing material.

The agent may comprise a single type of component or a blend of components. Preferably, the agent is selected from one or more medicinal agents and drugs. If desired, the agent may further comprise flavoring agents, surfactants, water, alcohol or other solvents provided that such additives are compatible with the agents and do not adversely impact stability.

The agent may be in the form of a liquid or in the form of finely divided particles. In one embodiment, the agent is in the form of finely divided particles having diameters ranging from about 1 micron to about 50 microns, more preferably, from about 2 microns to about 50 microns. In some embodiments, the agent can, for example, be dissolved in water or another solvent in which the agent is stable to dilute the dose of agent if, for example, the agent is a medicament that must be administered at very low doses. Alternatively, the agent could be dispersed in a material (e.g. a powder or particulate material) in which the agent is stable to dilute the dose of agent.

Preferably, the agent is provided in a pharmaceutically effective amount for the particular condition that the device is utilized for. For example, in one embodiment, the device is utilized to treat respiratory conditions such as bronchial asthma, and the agent is provided in a dose that ranges from about 5 μg to about 30 mg, more preferably, from about 10 μg to about 20 mg.

The device of the present invention can be used to deliver a variety of agents that can be used to systemically treat a variety of conditions. By way of example, some conditions that the device can be used to treat include, but are not limited to bronchial asthma, diabetes and cystic fibrosis. As such, the agent can include a variety of agents utilized to treat these conditions. For example, some conventional agents used to treat bronchial asthma include Albuterol, Serevent, Flovent, Ventolin, Singulair, Missing, Azmacort, Pulmicort, Accolate, Proventil and Atrovent. Any agents used to treat these and other conditions systemically can be used with the present invention.

In one embodiment, the agent may comprise two or more components housed within the container 10 as a blend. However, by blending certain components together, the shelf-life of the blend may, in some cases, be reduced. Thus, in another embodiment, where it is desirable to deliver the blend of components in one application or blast of propellant, it is preferred to provide a container 10 wherein the two or more agents are separated from each other until use. For example, this may be accomplished by providing a container 10 with layers of the agents separated by, for example, piercable material. Thus, in one embodiment, the container 10 has at its bottom end 13 a layer of piercable material, then a layer of an agent, then another layer of piercable material, then a layer of another agent, and so on, finally sealed at the top end 11 with a layer of piercable material. In such an embodiment, as the piercing member 12 passes through the container 10, it pierces the piercable material at the top end 11, passes through a first agent, pierces another layer of piercable material, passes through a second agent, and so on until the piercing member 12 exits the container 10 through the piercable material at the bottom end 13. The propellant then is expelled to capture the plurality of agents and deliver the blend of agents to the user.

In the manufacture of such embodiments, the container 10 is typically first sealed on one side 11 or 13 with a piercable sealing material. The first agent is then added to the container 10. A layer of piercable material then seals off the first agent. A second agent is then added to the container followed by another layer of piercable material. When each of the desired agents is added to the container 10, the container 10 is then hermetically sealed by sealing the other side 11 or 13 of the container 10 with a piercable sealing material.

The mechanism for exposing the agent in the container 10 to the propellant is shown in the various Figures in the form of a piercing member 12, particularly a needle or a blade. However, the mechanism is not particularly limited to such forms provided it is capable of allowing for the agent in the container 10, which is sealed, to be exposed to the propellant, released from the container 10 and carried out of the second end 6 of the body member 2 by the propellant into the mouth or nose of a user.

In one embodiment, mechanism is a piercing member 12 in the form of a needle having at least a hollow tip portion. As the needle pierces and passes through the container 10, the agent in the container 10 is picked up within the hollow portion of the needle and is carried towards the second end 6 of the body member 2. Propellant expelled from the aerosol canister then forces the agent from the needle, through the second end and into the mouth or nose of a user or to other bodily sites.

Preferably, the needle is substantially hollow along its length and is in line with the aerosol canister 8 such that propellant expelled from the aerosol canister 8 travels through the inside of the needle. As the propellant travels through the needle, it contacts and carries the agent within the needle out of the needle, through the second end and into the mouth or nose of the user.

The needle may be designed such that the hollow portion is sized and/or shaped so as to provide a precise dose of agent to a user. For example, the hollow portion may be sized and/or shaped to accommodate and pick up a precise dose of agent. Thus, for example, the diameter of the hollow portion of the needle may be made larger or smaller to accommodate more or less agent as the needle pierces and passes through the container 10.

The needle is not limited in its cross sectional shape and, for example, it may have a circular, oval, square, triangular, or other cross sectional shape. Preferably, the needle has a cross section substantially the same as the cross section of the portion of the container housing the agent, so as to minimize any residue of agent in the container 10.

In one preferred embodiment, the inner diameter of the hollow needle ranges from about 0.005" to about 0.1", more preferably, from about 0.01" to about 0.08". Of course, if the needle is not circular, the largest dimension of the cross section can be used to approximate the mean diameter for this purpose.

In another embodiment, the mechanism is a piercing member 12 in the form of a solid needle. In this embodiment, as the needle is moved through the container, it pierces the container 10 so as to provide a passageway through which propellant from the aerosol canister 8 may be expelled. Preferably, the solid needle is designed push the agent through and out of the container 10 as it passes through the container 10. The agent is then delivered to the mouth or nose of a user by the propellant, which is expelled from the aerosol canister 8 by actuation of the aerosol canister 8. The propellant passes around the solid needle, captures the agent, and carries the agent out of the second end and into the mouth or nose of a user. Preferably, the propellant is expelled with adequate force to cause substantially complete dispersion of the agent, and inhalation by the user directs the agent to the lungs of the user.

The solid needle is not limited in its cross sectional shape and, for example, it may have a circular, oval, square, triangular, or other cross sectional shape. In one embodiment, the needle has a cross section substantially the same as the cross section of the portion of the container 10 housing the agent, so as to minimize any residue of agent in the container 10. As such, the propellant expelled from the aerosol canister 8 may pass through the container 10 around the needle to capture and disperse the agent to the mouth or nose of a user. To provide greater passageway through which the propellant may pass to capture and disperse the agent, one or more bypass pathways 15 may further be formed through which propellant from the aerosol canister 8 may travel. For example, one or more bypass pathways 15 may be situated so as to direct propellant from the aerosol canister 8 towards the second end 6 of the body member 2 where the needle pushes the agent from the container 10. The propellant, thus, travels through the one or more bypass pathways 15 to the second end where it meets up with the agent from the container and disperses the agent into the mouth or nose of a user.

Alternatively, the needle may be sized with a cross section smaller than the cross section of the portion of the container 10 housing the agent such that the propellant may be expelled through the portion of the container housing the agent around the outer surface of the needle. In this embodiment, the one or more bypass pathways 15 may also be used provide additional space through which propellant may travel. Thus, the propellant may be expelled both around the outer surface of the needle and through the one or more bypass pathways 15.

In another embodiment, the mechanism is a piercing member 12 in the form of a blade having a cross section less than the cross section of the portion of the container 10 housing the agent. As the blade pierces the container 10, an opening is formed. Aerosol is then expelled around the outer surface of the blade and through the opening formed by the blade, thereby carrying the agent out of the container 10, through the second end and into the mouth or nose of a user.

In one embodiment, the agent within the container 10 is sealed at the top and/or bottom of the container 10 by a conventional piercable material such as, for example, a plastic or metal film or combinations of plastic and metal films as described above, to ease piercing of the container 10 and to enable further opening up of the opening formed by the blade in the container 10. Thus, as the propellant is forced around the blade through the opening formed by the blade, the force of the propellant against the piercable material surrounding the opening further opens up the piercable material and assists in carrying the agent out of the container 10. This embodiment is not limited to use with the blade and, for example, in any embodiment wherein the piercing member 12 is smaller in cross section than the cross section of the portion of the container 10 housing the agent, the container may be sealed with a piercable material or the like that promotes further opening up of the opening formed by the piercing member 12 in the container 10.

The blade is not limited in cross sectional shape and it may, for example, have an “X”-shaped, “T”-shaped, “U”-shaped or linear shaped cross section to provide openings in the form of an “X”, a “T”, a “U” or a slit, respectively. It is believed that any of these blade shapes will provide an opening wherein pressure of the propellant expelled from the aerosol canister 8 will have a tendency to further open up the opening formed by the blade to facilitate escape of the agent out of the container 10.

The piercing member 12 is preferably designed to avoid cutting a piece of the container 10 or piercable material free as it pierces and passes through the container 10, thereby preventing ingestion of the container 10 or piercable material. This may be accomplished by, for example, providing a piercing member 12 that is sharpened at the piercing end to about a 30° to 60° angle and blunted at the rim of the piercing member 12 opposite the apex of the point. With such an arrangement, the piercing member 12 leaves the pierced portion of the container 10 or piercable material “hinged” to the container 10. This can further be accomplished by fabricating the piercable material of one or more layers of aluminum foil and one or more layers of polyester, polyolefin and/or polypropylene film as set out above. In such embodiments, the plastic layer(s) assists in preventing the seal from becoming completely detached from the container as the piercing member 12 passes through the seal. Rather, with such an arrangement, the piercing member 12 leaves the piercable material “hinged” to the container 10. Further, in some embodiments, by forming the piercing member 12 smaller than the cross section of the portion of the container housing the agent and smaller than the piercable material sealing the portion of the container 10 housing the agent, the piercable material is further prevented from becoming cut free as the piercing member 12 pierces and passes through the container 10.

In each of the embodiments of the piercing member 12, it may be desirable to include one or more bypass pathways 15 situated so as to divert a portion of the propellant around the piercing member 12 and around the portion of the container 10 housing the agent. Thus, for example, a portion of the propellant expelled from the aerosol canister may pass through the piercing member 12 and/or around the outer surface of the piercing member 12 through the portion of the container housing the agent, and a portion of the propellant may pass through the one or more bypass pathways 15. The bypass pathways 15 in conjunction with the propellant passing through and/or around the piercing member 12, then expel the propellant towards the second end 6 where the propellant can capture the agent from the container 10 and assist in dispersing the agent into the mouth or nose of a user. Such bypass pathways 15 are shown, for example, in FIGS. 4–8.

In a preferred embodiment, the bypass pathways 15 are included in delivery devices wherein the piercing member 12 is in the form of a hollow needle. Preferably, in embodiments wherein the inner diameter of the hollow needle is smaller than the size of the portion of the aerosol canister 8 through which the propellant is expelled (e.g. the valve stem 13), the propellant expelled from the aerosol canister 8 may be in excess of the amount that can pass through the hollow needle at a given time. This may cause backup of the propellant and a reduction in the force of the propellant as it passes from the aerosol canister through the device. In this embodiment, inclusion of the one or more bypass pathways 15 provides additional areas through which the propellant from the aerosol canister 8 may pass, thereby eliminating backup of the propellant at the needle and eliminating reduction in the force of the propellant as it passes from the aerosol canister 8 through the device and out of the second end 6. Inclusion of the bypass pathways 15 may be advantageous in certain embodiments where it is desirable to utilize hollow needles with small diameters, for example, where it is desirable to deliver a small does of agent and the size of the hollow needle determines the size of the dose delivered.

In an alternative embodiment, the mechanism for exposing the agent in the container to the propellant is the force of the propellant against the sealed container 10. In some embodiments, the device is designed such that the force of the propellant against the sealed container removes or opens the seal on the container 10, thereby releasing the agent from the container 10 and carrying the agent out of the second end 6. In one embodiment, for example, the propellant would be expelled to hit the container 10, thereby causing the seal to open. The propellant would then force the agent through the container 10 and through the seal at the bottom of the container 10. Preferably, a channel 50 or similar sealing mechanism, such as that shown in FIG. 15, would be included that extends from the aerosol canister 8 directly to the surface of the sealed container 10. This channel 50 would preferably be formed so that the propellant is directed solely through the container 10 to prevent the propellant from opening the sealed container 10 and allowing the agent to flow upwards out of the container 10 towards the aerosol canister rather than through the container 10 towards the second end 6 to the user. One such embodiment is shown, for example, in FIG. 15, wherein the channel 50 is formed between the holding member 20 and a stop block or cover 52 that is placed over the container 10 and holding member 20. The formation of the channel 50 is not limited to this embodiment and other means of forming channels 50 could be used. The channel 50 is sized to precisely surround the portion of the container 10 housing the agent and is positioned directly against the surface of the container 10 to provide a sealed pathway from the aerosol canister to the container 10. This channel 50, in some embodiments, could comprise the valve stem 13 of the aerosol canister 8. When the valve stem comprises the channel, the valve stem 13 is the same size or larger than the portion of the container 10 housing the agent and the valve stem forms a seal over the portion of the container 10 housing the agent, such that the propellant is directed solely through the portion of the container 10 housing the agent and propellant is prevented from flowing upwards and allowing the agent to flow upwards out of the container 10 towards the aerosol canister.

Figure 5:
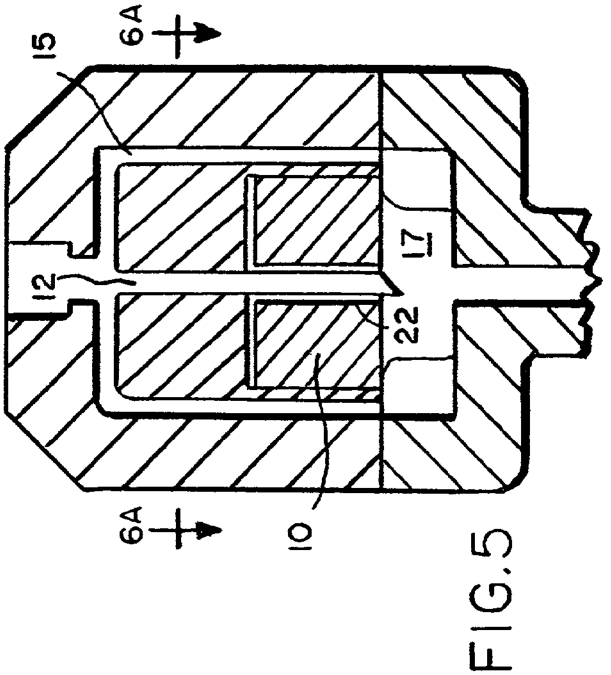
FIG. 5 is an enlarged cross-sectional view of FIG. 4 excluding the aerosol canister.
Figure 4:
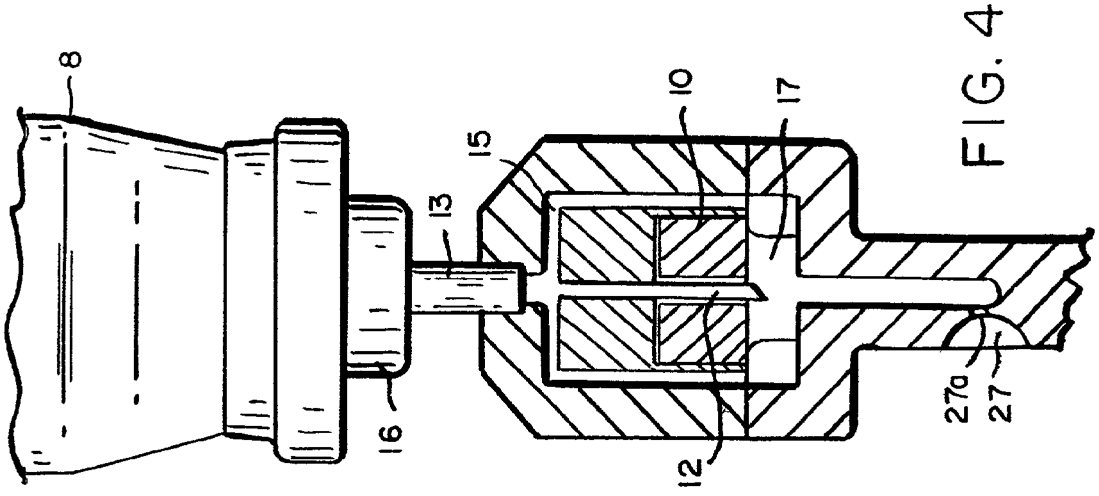
FIG. 4 is a cross-sectional view of the components inside the body member in accordance with another embodiment of the delivery device wherein the delivery device includes a plurality of bypass channels.
Figure 7:
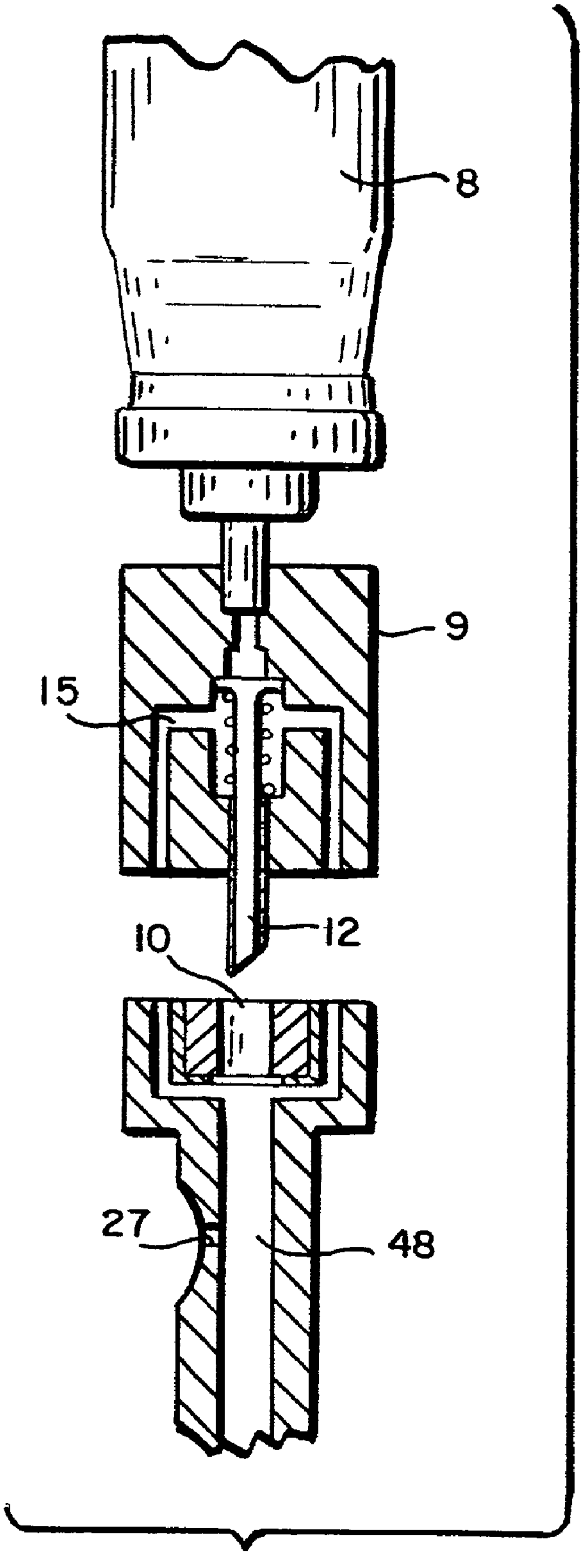
FIG. 7 is a side cross-sectional view of the components inside the body member in accordance with another embodiment of the delivery device wherein the delivery device includes a plurality of bypass channels and wherein the device is shown with the top portion separated from the bottom portion.

In one embodiment, as shown in FIGS. 4 and 5, a swirl chamber 17 or similar compartment is located within the body member 2 between the container 10 and the second end 6. The piercing member 12 pierces and passes through the container 10 and propellant expelled from the aerosol canister 8 passes through the container 10 and/or through the bypass pathway(s) 15. Propellant and agent travel through the container 10 into the swirl chamber 17 and propellant from the bypass pathway(s) 15 is deposited into the swirl chamber 17 where it assists in breaking up the agent and distributing the agent within the propellant. Increased passageways, through which additional propellant may flow through, may be beneficial in some applications because it can provide enhanced dispersement of the agent into the mouth or nose of a user. Preferably, the propellant captures and disperses the agent into the mouth or nose of a user and inhalation by the user directs the agent to the lungs of the user.

Figure 10:
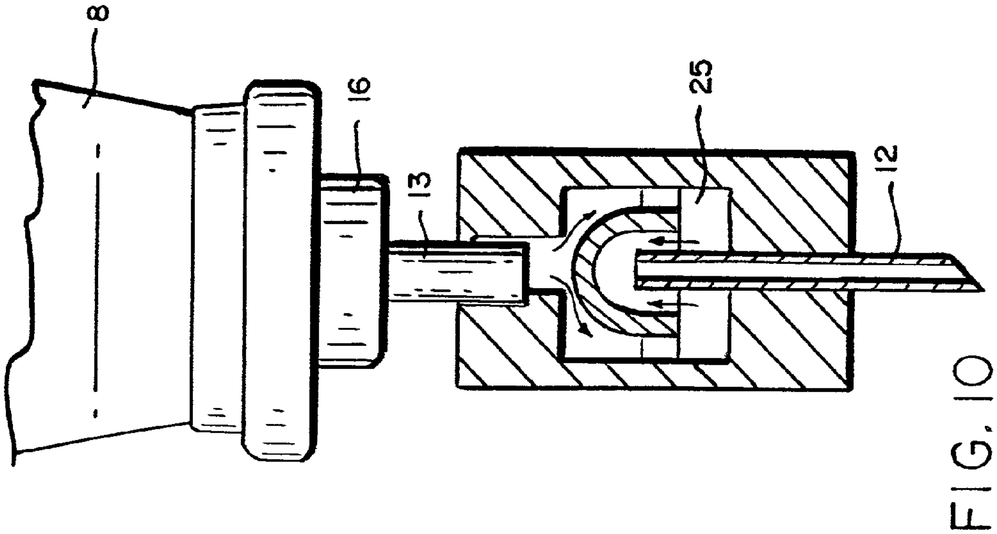
FIG. 10 is an enlarged view of the device shown in FIG. 9.
Figure 9:
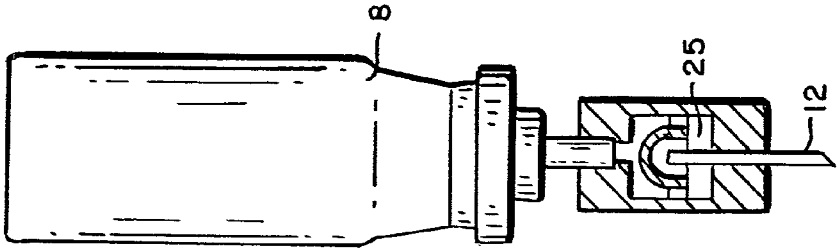
FIG. 9 is a cross-sectional view of the components inside the body member in accordance with another embodiment of the delivery device wherein the delivery device includes an expansion chamber.

As shown in FIGS. 9–10, the device may further include an expansion chamber 25 positioned between the aerosol canister 8 and the container 10. The propellant housed within the aerosol canister 8 is typically in a liquid state and, as it is expelled from the aerosol canister 8, it expands to a gaseous state. The expansion chamber 25 may further be included in the device to provide a space wherein the propellant may expand to a gaseous state before it passes through the container 10 and captures the agent.

A nozzle 27 or similar mechanism is located in between the second end 6 of the body member 2 and the container 10. The nozzle 27 assists in regulating and directing the flow of the propellant and agent through the second end 6 of the body member 2 and into the mouth or nose of the user. Nozzle 27 includes an orifice **27*a*. Orifice 27*a*** typically will have a diameter of from about 0.010 to 0.060 inches, preferably 0.012 to 0.020 inches. However, dimensions outside these ranges may be useful in delivering particular agents.

The device may further include a sealing mechanism 19 positioned between the aerosol canister 8 and the container 10 for sealing off the passageway of the propellant expelled from the aerosol canister 8 through the container 10 so as to prevent escape of propellant and to direct the propellant through the container 10 and/or bypass pathway(s) 15. For example, as shown in FIG. 2, the sealing mechanism 19 may form a tunnel-like pathway between the portion of the canister through which the propellant is expelled and the container 10. Thus, as the propellant exits the aerosol canister 8, it travels solely through the tunnel-like pathway and through the container 10 thereby eliminating what is commonly referred to as "blow-by."

Aerosol canisters are well known and, thus, although described and shown with reference to a preferred embodiment, the general features (e.g. size, shape, materials) of the aerosol canister 8 may be in accordance with conventional aerosol canisters.

One embodiment of the aerosol canister 8 is shown in FIG. 3. As shown, the aerosol canister 8 has a valve stem 13 extending from its bottom end. The valve stem 13 may be connected to the aerosol canister 8 via a collar 16 or similar connection mechanism. The valve stem 13 is movable within the aerosol canister 8 such that as pressure is applied to the valve stem 13 in a direction towards the aerosol canister 8, the valve stem 13 is depressed within the aerosol canister 8. This may be accomplished by, for example, a stop member 9 positioned between the aerosol canister 8 and container 10, such that the aerosol canister 8 contacts the stop member 9 as the aerosol canister 8 is moved downwards towards the container 10. Located through a side wall of the valve stem 13 is an aperture 31. When the valve stem 13 is in its normal state extending out of the aerosol canister 8, as shown in FIG. 8, the aperture 31 is located outside the aerosol canister 8. As pressure is applied to the valve stem 13 and the valve stem 13 is depressed into the aerosol canister 8, the aperture 31 enters the aerosol canister 8, thereby actuating the aerosol canister 8. Upon actuation, the propellant within the aerosol canister 8 is driven out of the aerosol canister through the aperture 31 and through the valve stem 13.

The propellant may be selected from those used in the art such as, for example, liquid chlorofluorocarbons (CFCs), which include fluorotrichloromethane, dichlorodifluoromethane and dichlorotetrafluoroethane. However, because CFC's are believed to be destructive of the ozone layer, hydrofluorocarbons (HFCs) such as, for example, 1,1,1,2-tetrafluoroethane (also commonly referred to as propellant 134a, HFC-134a, and HFA-134a) and 1,1,1,2,3,3,3-heptafluoropropane (also commonly referred to as propellant 227, HFC-227, and HFA-227), are preferred because they are believed to be more ozone friendly than CFC's.

In addition to propellants, the aerosol canister 8, if desired, may also contain a variety of agents. For example, the aerosol canister 8 may further house an agent in suspension or solution. The agent in suspension or solution may be, for example, selected from flavoring agents, surfactants, water, alcohol or other solvents, and medicinal agents.

The aerosol canister 8 may be prepared by conventional methods such as, for example, pressure filling or cold filling the propellant into the canister. Such methods are well known to those skilled in the art. Conventional valves, preferably metering valves, are used to deliver the propellant of the present invention. Such metering valves deliver a particular amount of propellant per actuation. Thus, the use of metering valves may be desirable to automatically provide the desirable amount of propellant required for a particular application. Preferably, the aerosol canister 8 having a metering valve contains an amount of propellant for multiple uses.

It is also possible to use other types of valves such as, for example, open flow type valves. Such valves allow for expulsion of the contents of the can for as long as the valve is depressed. Preferably, because it is possible with such valves to deliver an excessive amount of propellant, such aerosol canisters 8 of this form are single-use pressurized containers holding an amount of propellant suitable for a single use. Thus, after a single use, the aerosol canister 8 is either replaced or the device thrown out.

In a preferred embodiment, the aerosol canister 8 is movable within the body member 2 towards the container 10 and the piercing member 12 is situated such that, as the aerosol canister 8 is moved towards the container 10, the piercing member 12 likewise moves towards the container 10. For example, the piercing member 12 may be directly mounted to the aerosol canister 8 via the valve stem 13. In another embodiment, as shown in FIGS. 1, 2, 7 and 8, a spring 29 and pin 30 mechanism connects the piercing member 12 to the valve stem 13. In such an embodiment, as the aerosol canister 8 is depressed downwards within the body member 2 towards the container 10, the spring 29 is compressed and the piercing member 12 pierces and passes through the container 10. The aerosol canister 8 is actuated and propellant is expelled. Then, when the user releases the aerosol canister 8, the spring 29 and pin 30 mechanism acts to bring the aerosol canister 8 back upwards in the body member 2 to its start position.

Figure 18B:
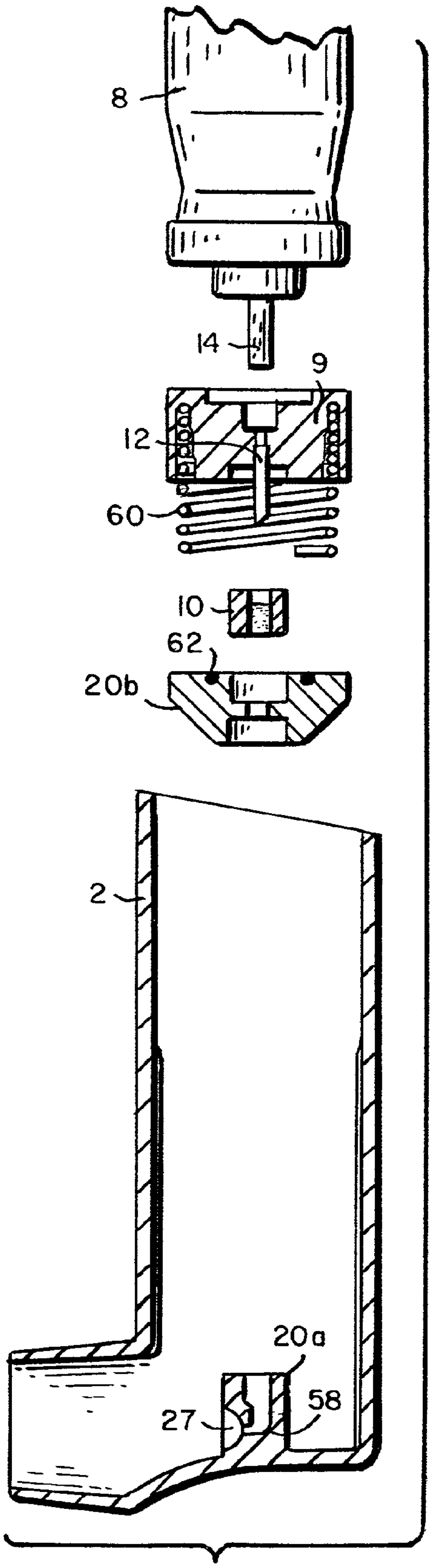
FIGS. 18*b–e* show the steps of using the delivery device in accordance with another embodiment of the present invention.
Figure 18C:
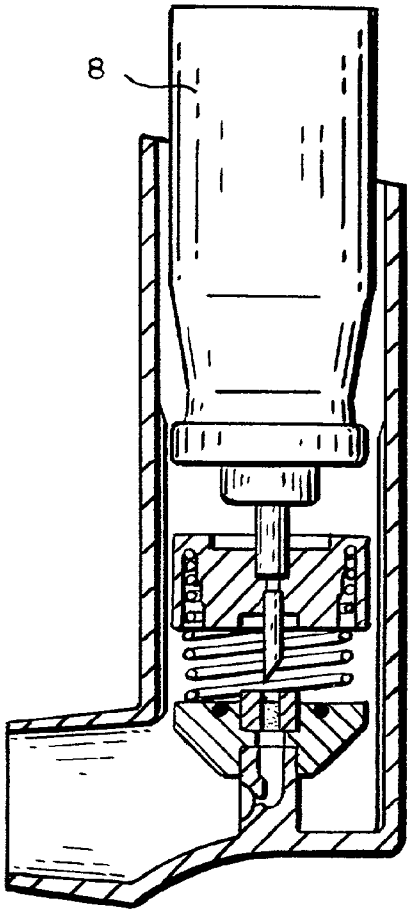
Figure 18D:
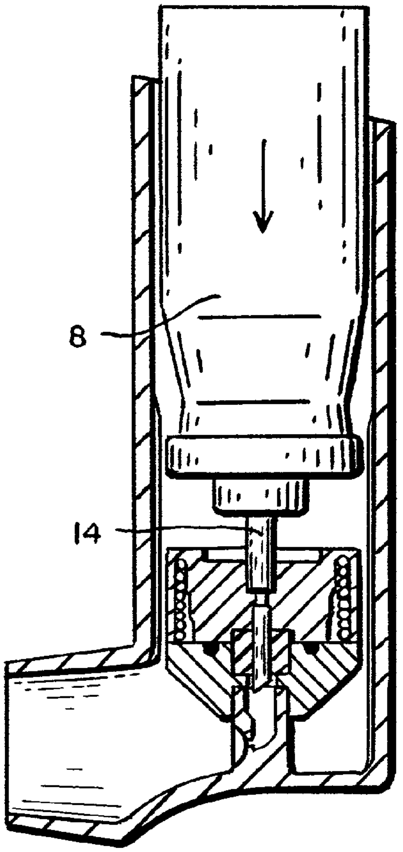
Figure 18E:
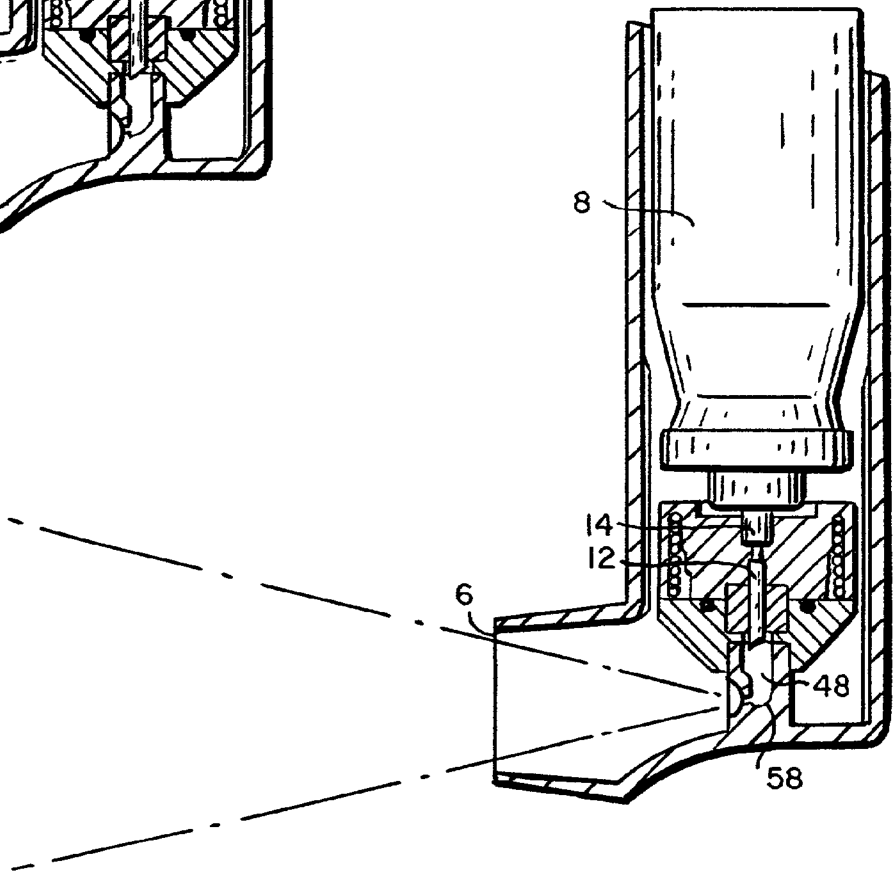

In another embodiment, as shown in FIGS. 18*b–e*, a stop member 9 is positioned between the aerosol canister 8 and the container 10 housing the agent. A spring 60 or similar mechanism is further situated between the stop member 9 and the container 10. The container 10 can be held within the body member 2 by a holding mechanism comprising a lower portion 20*a* and an upper portion 20*b* which fit together and which hold the container 10 as shown in FIGS. 18*b–c*. The nozzle 27 is preferably located in the lower portion 20*a* of the holding mechanism, through which the agent and propellant are expelled from the device. Prior to use, the delivery device 1 is configured as shown in FIG. 18*c*, with the valve stem 14 positioned in the stop member 9 and the spring expanded to separate the piercing member 12 from the container 10. The device can then be actuated by pushing the aerosol canister 8 downwards towards the container, as shown in FIG. 18*d*. As the aerosol canister 8 is moved downwards, the stop member 9 is also pushed downwards, thereby compressing the spring 60. The piercing member 12 passes through the container 10 and picks up the agent. As the aerosol canister 8 is moved further downwards, the valve stem 14 is pushed upwards into the aerosol canister 8, as shown in FIG. 18*e*, thereby actuating the aerosol canister 8 to expel propellant. The propellant passes through the piercing member 12 (also around the piercing member and/or through bypass pathways 15 in some embodiments), captures and disperses the agent out of the second end 6 of the device. As shown in FIG. 18*e*, the lower portion 20*a* of the holding mechanism may include a lumen 48 through which the propellant and agent pass and exit through nozzle 27, which directs the propellant and agent through the second end 6.

In one embodiment, the valve stem 13 of the aerosol canister 8 is the piercing member. Thus, in this embodiment, as the aerosol canister 8 is moved downwards, the valve stem 13 pierces and passes through the container 10. The valve stem 13 may be hollow such that as the valve stem 13 pierces and passes through the container 10, agent is picked up within the valve stem 13. The aerosol canister 8 is then actuated and propellant is expelled through the hollow valve stem 13, thereby capturing and dispersing the agent out of the valve stem 13 and into the mouth or nose of a user. Preferably, in this embodiment, the valve stem 13 is designed with a cross section substantially the same as the cross section of the portion of the container housing the agent, so as to minimize any residue of agent in the container 10. The valve stem 13 and/or portion of the container 10 housing the agent may further be designed so as to accommodate a precise dose of agent.

Alternatively, it is possible to provide as a piercing member a valve stem 13 with a cross section substantially the same as the cross section of the portion of the container 10 housing the agent and a narrow hollow portion such that as the valve stem 13 pierces and passes through the container 10, the agent is pushed through the container 10 rather than or in addition to being picked up within the valve stem 13. Then, upon actuation of the aerosol canister 8, propellant expelled through the valve stem 13 contacts and disperses the agent picked up in the valve stem and/or pushed through the container 10 into the mouth or nose of a user.

In some embodiments, wherein the valve stem 13 is the piercing member 12, the valve stem 13 can be sharpened at the piercing end to facilitate piercing of the container 10 and to avoid cutting a piece of the piercable material free as it pierces and passes through the container 10. As set out above, for example, the piercing member, in this embodiment, the valve stem 13, can be sharpened to about a 30° to 60° angle and blunted at the rim of the piercing member 12 opposite the apex of the point.

The device of the present invention is particularly superior to other devices in that it delivers a very high emitted dose of the agent from the container 10. As used herein, "emitted dose" is defined as the percentage of the agent housed in a single dose compartment 22 of the container 10 that is emitted from the device during use.

The exceptionally high emitted dose using the device of the present invention is achieved by the present invention by reducing the amount of residue that collects and remains in the device. This can be accomplished in a number of ways.

In some embodiments wherein the mechanism comprises a piercing member 12 in the form of a hollow needle, the hollow piercing member 12 has an outer diameter that is approximately the same size as the diameter of the compartment 22 housing the agent. This minimizes the amount of agent that collects between the outer diameter of the piercing member 12 and the walls of the compartment 22 as the piercing member passes through and picks up the agent. Further, the thickness of the piercing member 12 wall (i.e. the distance between the outer diameter of the hollow piercing member and the inner diameter of the hollow piercing member) is preferably minimized so that as the piercing member 12 passes through the container 10, most if not all of the agent is picked up inside the hollow of the piercing member 12. Further, any agent not picked up inside the hollow of the piercing member 12 is pushed through the container by the walls of the piercing member. In this embodiment, because the piercing member 12 has an outer diameter that is approximately the same size as the diameter of the compartment 22 housing the agent, approximately all of the agent from the compartment 22 is either picked up within the hollow of the piercing member 12 or pushed out of the compartment 22 by the walls of the piercing member. Agent collected between the outer diameter of the piercing member 12 and the compartment 22 walls is minimized.

Likewise, in some embodiments wherein the mechanism is a solid piercing member 12, the piercing member 12 has an outer diameter that is approximately the same size as the diameter of the compartment 22 housing the agent. This minimizes the amount of agent that collects between the outer diameter of the piercing member 12 and the compartment 22 walls as the piercing member passes through the compartment 22. As the solid piercing member 12 passes through the compartment 22, approximately all of the agent is pushed through the compartment towards the second end of the device by the piercing member 12. Agent collected between the outer diameter of the piercing member 12 and the compartment 22 walls is minimized.

Figure 16A:
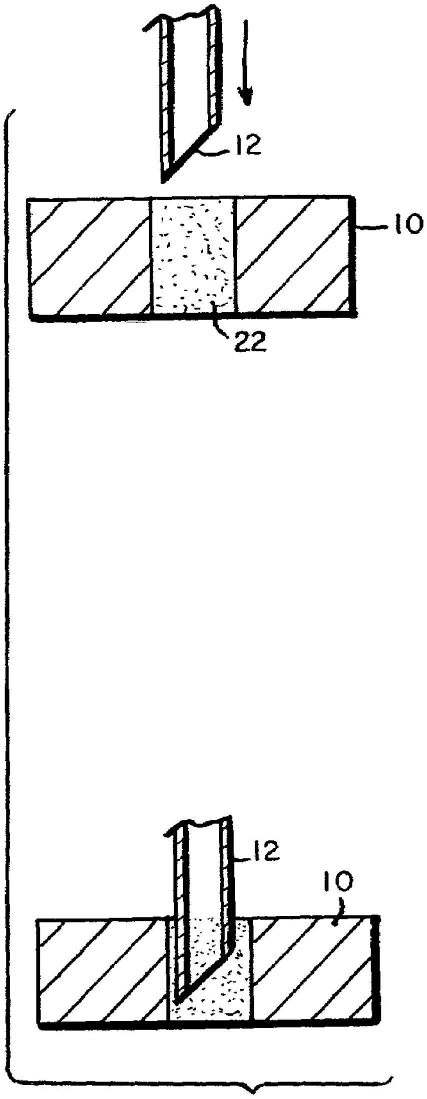
FIG. 16*a–b* show embodiments of the piercing member passing through the compartment in the container while providing clearance between the piercing member and one or both sides of the compartment.
Figure 16B:
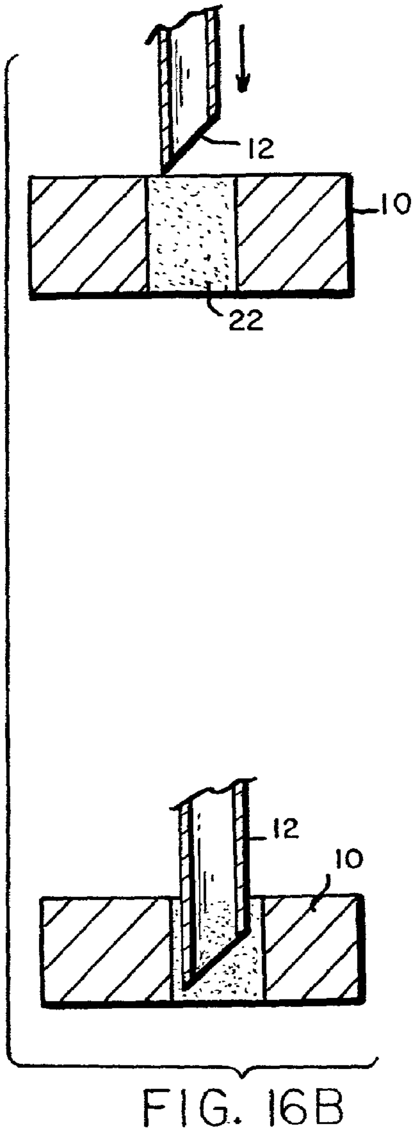

During use, as the piercing member 12 passes through the container 10, it first pierces and passes through the piercable material that seals the agent in the container 10. Preferably, the piercable material is pierced but remains connected to the container 10 to prevent the piercable material from being pushed out of the second end 6 of the device into the mouth or nose of the user. The piercable material is described above and, preferably, is formed of one or more thin layers of material (e.g. polyester, aluminum foil, polyolefin and polypropylene. The thickness of the piercable material is preferably no greater than about 0.004 inch, more preferably, between about 0.001 and about 0.003 inch, and more preferably, between about 0.001 and about 0.0015 inch. In some embodiments, to prevent the piercable material from becoming separated from the container as the piercing member 12 passes through, some clearance space is preferably provided between the piercing member 12 and the walls of the compartment 22 housing the agent. This clearance space allows the piercable material to be pushed up against the wall of the compartment 22 by the piercing member 12. If insufficient clearance is provided, then the piercable material may become separated from the container 10. Thus, a clearance at least as thick as the piercable material is preferably provided between the piercing member 12 and the inner walls of the compartment 22. In other words, the piercing member 12 is preferably slightly smaller than the diameter of the compartment 22 housing the agent by at least the thickness of the piercable material. The clearance space can be provided on one side of the piercing member 12 as it passes through the compartment 22 or it can be provided on both sides of the piercing member 12. For example, if the piercable material is 0.001 inch thick, then the piercing member 12 could be about 0.001 smaller in diameter than the diameter of the compartment 22 and the piercing member 22 would be aligned to pass through the compartment 22 with at least about 0.001 inch clearance on one side of the compartment and approximately no clearance on the other side of the compartment 22, for example, as shown in FIG. 16*a*. Alternatively, for example, if the piercable material is 0.001 thick, then the piercing member 12 could be at least about 0.002 smaller in diameter than the diameter of the compartment 22 and the piercing member 12 would be aligned to pass through the center of the compartment 22 with at least about 0,001 inch clearance on each side of the compartment 22, for example, as shown in FIG. 16*b*.

In some of the embodiments, it is desirable to include a guiding mechanism that ensures that the piercing member 12 passes through the container 10 precisely where intended. The guiding mechanism could, for example, ensure that the piercing member 12 passes precisely through the center of the compartment 22 or in any other place within the compartment. For example, in the embodiment above where the piercable material is 0.001 inch thick and the piercing member 12 is at least about 0.002 inch smaller in diameter than the diameter of the compartment 22, the guiding mechanism could ensure that the piercing member 12 is aligned to pass through the center of the compartment 22 with at least 0.001 inch clearance space on each side of the compartment 22. In the embodiment above where the piercable material is 0.001 inch thick and piercing member 12 is at least about 0.001 inch smaller in diameter than the diameter of the compartment 22, the guiding mechanism could ensure that the piercing member 22 is aligned to pass through the compartment 22 with at least about 0.001 inch clearance space on one side of the compartment 22 and approximately no clearance on the other side of the compartment 22.

Figure 17B:
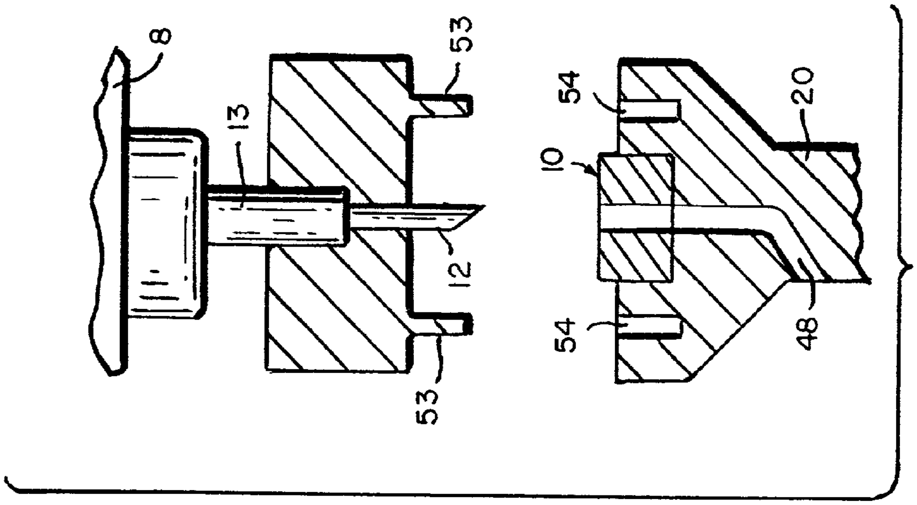
FIG. 17*b* shows an enlarged view of the guiding mechanism of FIG. 17*a*.
Figure 17A:
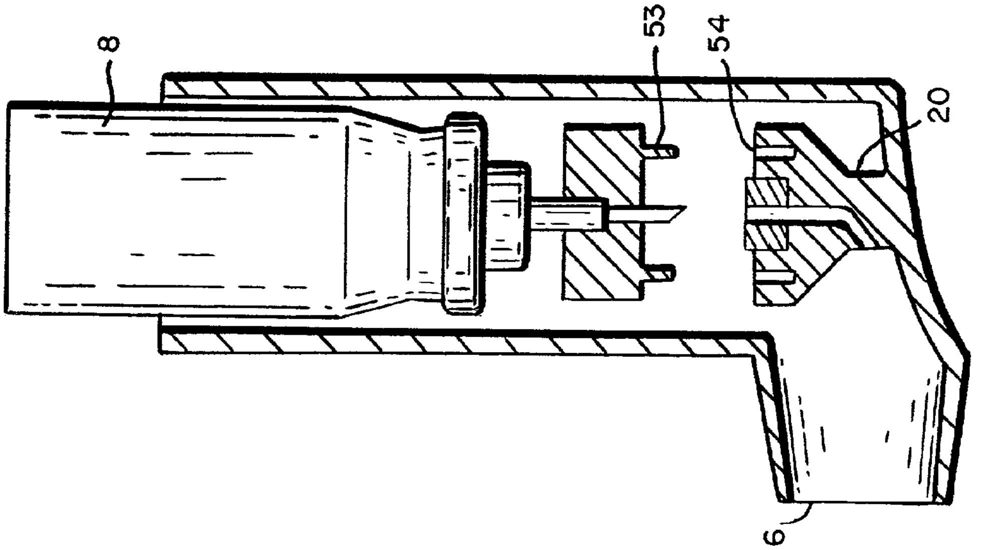
FIG. 17*a* shows another embodiment of the delivery device of the present invention wherein the device includes a guiding mechanism that guides the piercing member through a precise location in the container, wherein the guiding mechanism is in the form of one or more pins and corresponding grooves that line up when the piercing member is precisely aligned with the desired location in the container.
Figure 18A:
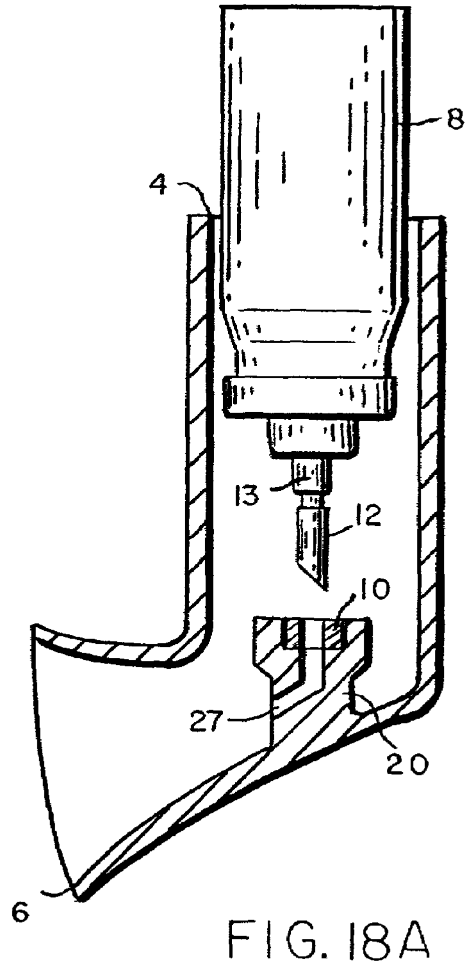
FIG. 18*a* shows another embodiment of the delivery device of the present invention wherein the second end of the device is enlarged or flared.

In one embodiment, the guiding mechanism is in the form of one or more pins 53 and corresponding apertures 54 located within the device, for example, as shown in FIG. 17. Thus, for example, one or more pins 53 (or apertures) could be located on a portion of the device that moves downwards as the source of negative pressure and piercing member 12 are moved downwards and one or more apertures 54 (or pins) could be located near the container 10. As the source of negative pressure and piercing member 12 are moved downwards, the pins 53 will slide into the apertures 54 when properly lined up. If the alignment is off, the pins 53 and apertures 54 will prevent further downward movement and will assist in realigning the device so that the pins 53 and openings 54 line up. In a particularly preferred embodiment, two pins 53 and two corresponding apertures 54 are located in the device, for example, as shown in FIG. 17, for aligning the piercing member 12 to pass through the proper portion of the container 10.

The amount of residue that is collected and remains within the compartment 22 after use, e.g. along the side walls of the compartment 22, can be further eliminated by providing an aerosol canister that expels propellant not only through the hollow piercing member 12 but also through the compartment 22 around the piercing member 12.

In some embodiments, the amount of residue that is collected and remains in the device is further reduced by designing the second end 6 ("mouthpiece") accordingly. In general, the second end 6 is designed to inhibit collection of residue along the surfaces. For example, in some embodiments, the second end 6 through which the agent and propellant exit the device and enter the user's mouth is enlarged. When the propellant and agent exit the second end 6, the stream of the propellant and agent is believed to expand into a generally conical-like shape. Thus, by forming the second end 6 to prevent impingement of the propellant and agent against the inner walls of the second end 6, collection and residue can be minimized. This can be done, for example, by forming the sides of the second end 6 to flared outwards, for example, as shown in FIG. 18

The collection of residue in the device is further minimized by eliminating potential surfaces and crevices within the device where the agent can collect. In one preferred embodiment shown in FIG. 20, accumulation is reduced by having piercing member 12 stop just above a curved surface 58 that sweeps down towards nozzle 27 as shown in FIG. 20*c*. This is also shown in FIG. 18.

Figure 20B:
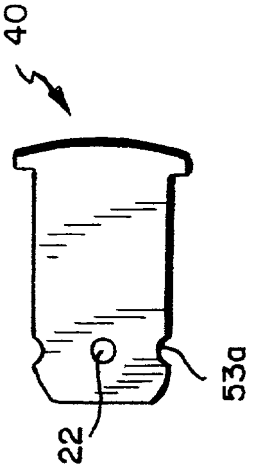
FIG. 20*b* shows a top view of the drawer-like holding member of FIG. 20*a*.
Figure 20A:
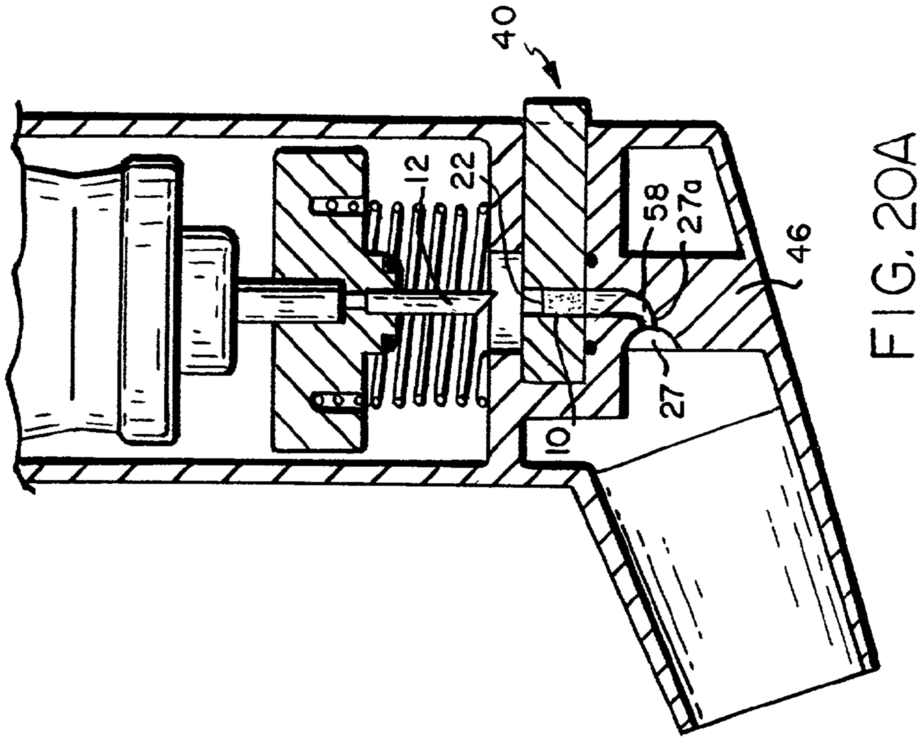
FIG. 20*a* shows a cross-section side view of another embodiment of the delivery device of the present invention wherein the device includes a guide mechanism that guides the piercing member through a precise location in a drawer-like holding member including the container for the agent, wherein the guiding mechanism is in the form of one or more pins and corresponding holes and grooves that line up when the piercing member is precisely aligned with the desired location in relation to the container.
Figure 20C:
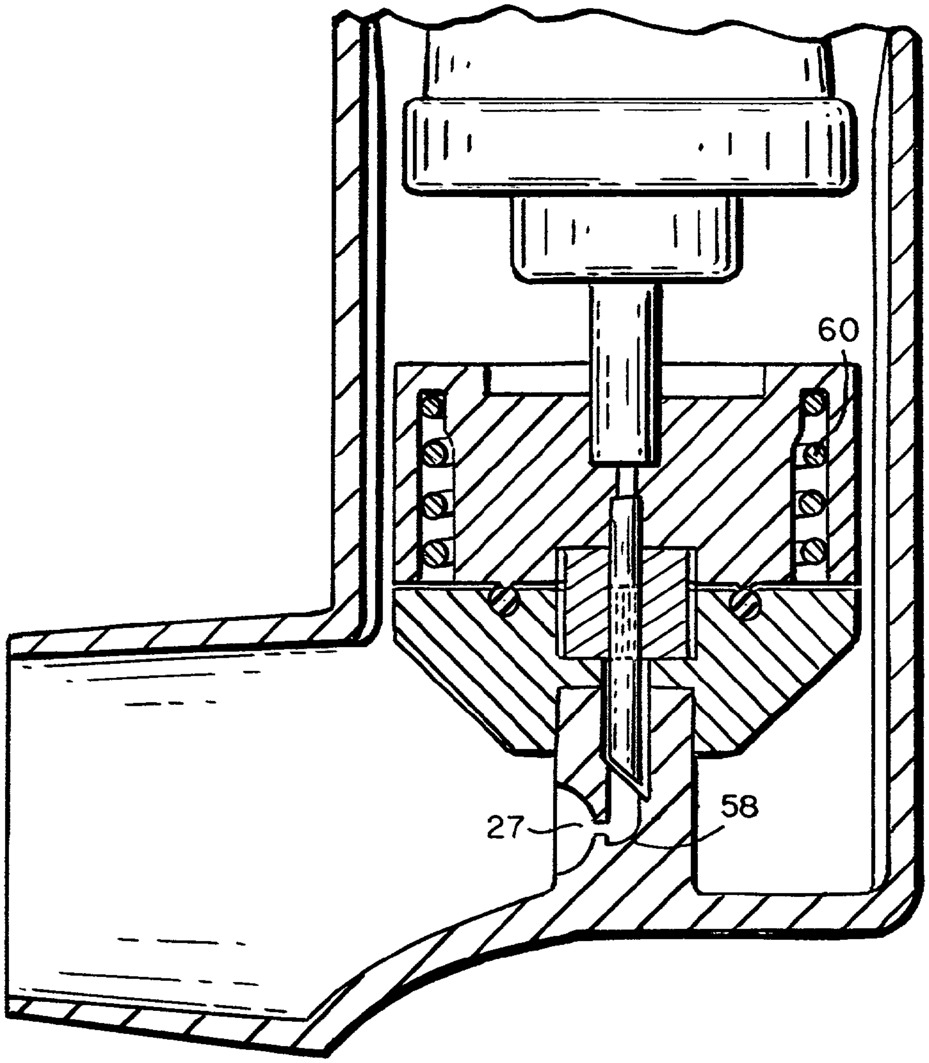
FIG. 20*c* is an enlarged cross-section view of the device of FIG. 20*a* in the discharge position wherein the needle has passed through the container in the drawer-like member and is stopped at the top of a curved section adjacent to the nozzle.

Further, when the piercing member 12 is passed through the container 10 and the propellant expelled to drive the agent through the second end 6, the piercing member 12 is preferably positioned at the top of the radius of curved surface 58, as shown in FIG. 20. This further minimizes the collection of agent within the inner surfaces of the device.

Figure 21A:
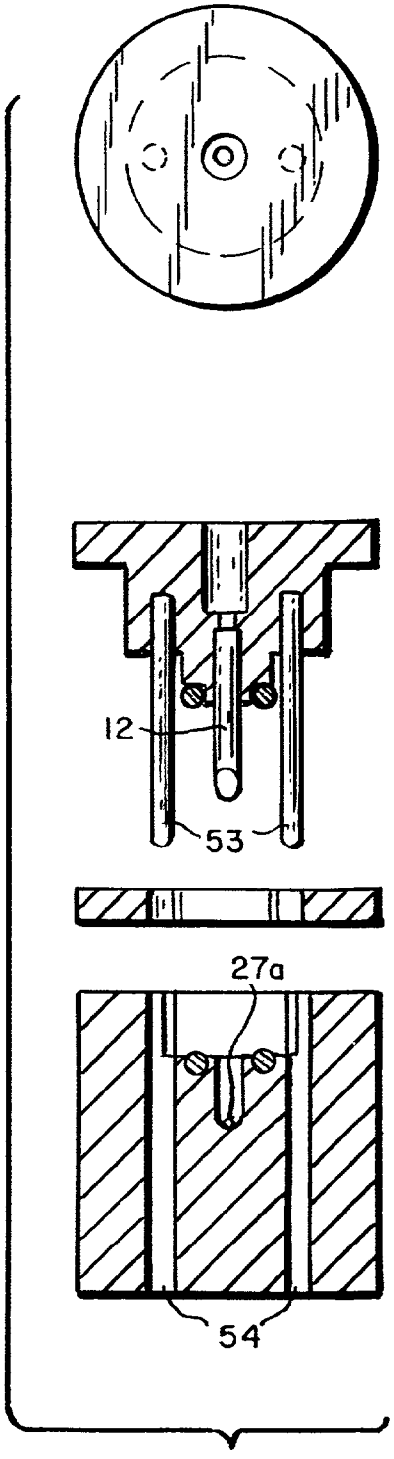
FIG. 21*a* is an exploded cross-section front view of the device shown in FIG. 20, showing guide pins and apertures for accepting the pins.
Figure 21B:
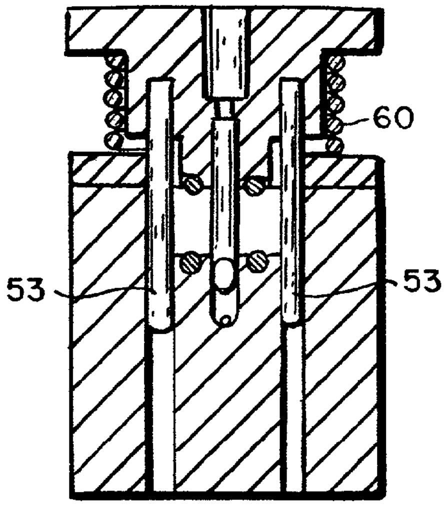
FIG. 21*b* is a cross-section front view of the device shown in FIG. 20 in the discharge position, wherein the needle has passed through the container and stopped.

In the device shown in FIG. 20, the drawer-like member is provided with a guiding mechanism in the form of one or more pins 53 and corresponding structure, e.g., apertures 54 shown in FIG. 21*a* to accept pins 53. Similar to the embodiment shown in FIG. 17, pins 53 pass through notches 53*a* in the drawer on either side of the container in order to perfectly align the passage of piercing member 12 through the aperture and thereby capture the maximum amount of agent. Guide pins 53 are longer than the needle, so that pins 53 pass through notches 53*a* to sufficiently secure drawer 40 before piercing member 12 passes through container 10 in drawer-like member 40. Piercing member 12 thus stops at radius 58 as shown in FIG. 20*c*, thereby centralizing piercing member 12 with great accuracy and thereby maximizing capture of the agent.

The collection of residue in the device can further be reduced by providing piercing member 12 or other mechanism with a beveled tip, as shown in FIG. 1, wherein the beveled tip is positioned to face the exit through which the propellant and agent exit the second end 6. This will direct the propellant and agent through the exit of the second end 6 so that the agent and propellant does not impinge on the inner surfaces of the second end 6.

Still further, collection of residue in the device is further minimized by providing highly polished inner surfaces of molded parts forming the device as opposed to machined surfaces.

The present device is capable of delivering particularly a high respirable fraction of agent. As used herein, the respirable fraction is the percentage of the dose that is delivered to the lungs. With prior delivery devices, a respirable fraction of less than 30% was possible. However, with the present invention, respirable fractions of greater than 30%, more preferably, greater than 35%, more preferably, greater than 40%, more preferably, greater than 45%, more preferably, greater than 50%, more preferably, greater than 60%, more preferably, greater than 65%, more preferably, greater than 70%, more preferably, greater than 75%, more preferably, greater than 80%, and even greater than 85% can be achieved.

The use of the delivery device 1 of the present invention can be further understood from the following discussion relating to a method for treating bronchial asthma and with reference to FIGS. 1–10.

To operate the device, a user places the second end 6 of the device near the bodily site. For example, when used to deliver the agent to the mouth or nose, the user inserts the second end 6 of the device into the mouth or nose. The user then presses the aerosol canister 8 downwards towards the container 10 within the body member 2 until the piercing member 12 pierces and passes through the container 10, thereby picking up and carrying the agent towards the second end 6 of the device. The aerosol canister 8 is actuated to expel propellant through the body member 2 towards the second end 6. The expelled propellant captures and disperses the agent into the mouth or nose of the user. During use, the propellant captures and disperses the agent into the mouth or nose of the user and inhalation by the user directs the agent to the lungs. When used to deliver the agent to other bodily sites, for example, to the ear of a user, the device is used as described above, without the user's inhalation to direct the agent.

The present invention also includes kits that comprise one or more delivery device 1 of the invention. Kits of the invention also may be include one or more containers 10 and aerosol canister 8 for use with the delivery device 1, and/or written instructions for use of the delivery device 1 and other components of the kit.

The delivery device 1 and methods of use of the present invention will be further illustrated with reference to the following Examples which are intended to aid in the understanding of the present invention, but which are not to be construed as a limitation thereof.

All documents mentioned herein are incorporated by reference herein in their entirety.

EXAMPLES

Figure 19:
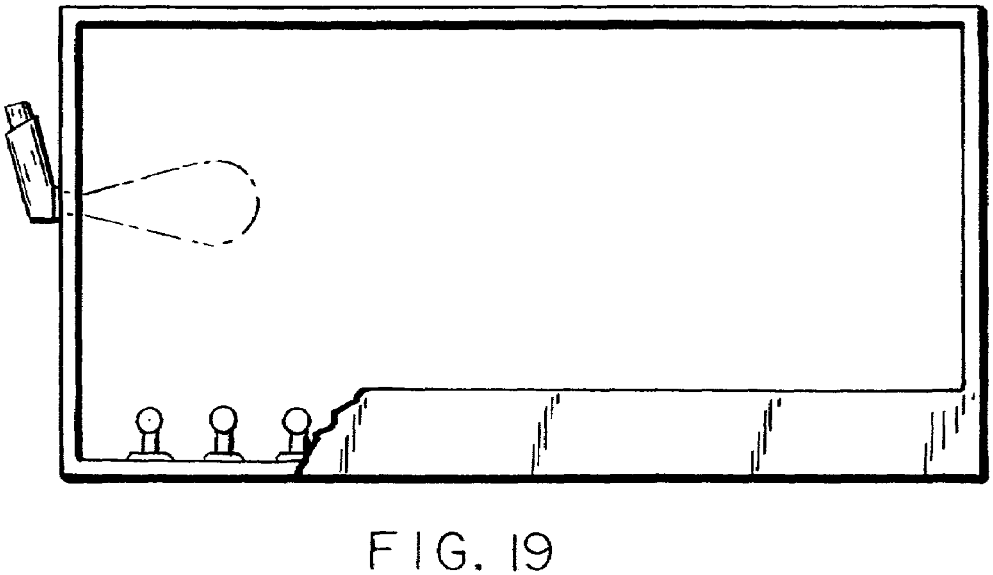
FIG. 19 shows the "black box" used in the Examples.

A number of tests were performed to analyze the dispersement of the propellant and agent out of the second end of the device. In these tests, the delivery device of the present invention was used to deliver the propellant with dispersed agent into a "black box" shown in FIG. 19. The black box comprises an elongate box approximately 2 feet long, 1.0 foot high and 1.0 foot wide. The black box has, at one end of its length, an opening through which the second end 6 of the device is inserted. Along the front of the black box is a short wall shielding a series of eight to ten lights from the camera lens and highlighting the powder stream discharged into the box. A camera on a tripod operating at, for example, approximately 300 frames/second, in some cases 3000 frames/second takes snapshots of the interior of the black box. The device of the present invention is actuated to dispel propellant and agent through the opening in the black box as the camera takes snapshots of the interior of the black box.

In each of the tests, the propellant with dispersed agent exits the second end 6 of the present device in the form of a soft, low velocity cloud. Further, when the device is used to deliver the propellant with dispersed agent into a large open space, e.g. a room, that is well lit, the propellant with dispersed agent exits the second end 6 of the present device in the form of a soft, low velocity cloud that remains suspended and remains visible for greater than about 3 seconds post actuation.

Without being bound by theory, it is believed that the suspension of the mixture by the present device provides a higher respirable fraction of agent. With prior devices, for example, the propellant and agent mixture is expelled from the devices in a high velocity, liner stream. This high velocity, linear stream impinges on the back of the mouth and throat of the user. With the present device, on the other hand, the mixture is delivered to the mouth in a soft, low velocity, cloud-like formation that remains suspended as the user inhales and directs the mixture down the throat to the treatment area (e.g. lungs).

The foregoing description of the invention is merely illustrative thereof, and it is understood that variations and modifications can be effected without departing from the scope or spirit of the invention as set forth in the following claims.

What is claimed is:

1. A device for delivery of at least one dose of an agent comprising:

a body member having at a first end a canister housing a propellant and a second end adapted for insertion into the mouth or nose of a user;

a container within the body member, for holding the dose of agent, wherein the container is positioned between the canister and second end; and a mechanism for exposing the dose of agent in the container to the propellant, the mechanism positioned between the canister and the container;

whereby as the canister is moved towards the container, (i) the mechanism passes through the container thereby carrying the dose of agent towards the second end, and (ii) the canister is actuated to expel the propellant and the dose of agent from the mechanism into the mouth or nose of the user.

2. A delivery device kit, comprising one or more of the delivery devices of claim 1 and one or more a containers each holding at least one dose of agent.

3. The device of claim 1, wherein the mechanism is sized to carry a precise dose of agent to the second end.

4. The device of claim 1, wherein the size of the mechanism controls the dose of agent delivered by the device.

5. The device of claim 1, wherein the mechanism is a piercing member.

6. The device of claim 5, whereby as the canister is moved towards the container, the piercing member passes through the container, thereby carrying the dose of agent towards the second end.

7. The device of claim 6, wherein at least the tip portion of the piercing member is hollow and the dose of agent is picked up within the hollow portion of the piercing member.

8. The device of claim 7, wherein the inner diameter of the piercing member is sized to pick up a precise dose of agent.

9. The device of claim 7, wherein the size of the inner diameter of the piercing member controls the dose of agent delivered by the device.

10. The device of claim 8, wherein the inner diameter of the piercing member ranges from about 0.005" to about 0.1".

11. The device of claim 8, wherein the inner diameter of the piercing member ranges from about 0.01" to about 0.08".

12. The device of claim 8, wherein the canister is connected to the piercing member such that the propellant is expelled from the canister through the hollow portion of the piercing member, thereby expelling the dose of agent from the piercing member.

13. The device of claim 5, wherein the piercing member is a needle.

14. The device of claim 5, wherein the piercing member is sharpened at the piercing end to about a 30° to 60° angle and the rim of the piercing member opposite the apex is blunted.

15. The device of claim 1, wherein the thickness of the container holding the agent controls the dose of agent delivered by the device.

16. The device of claim 5, wherein the container is partially filled with the dose of agent.

17. The device of claim 16, wherein the dose of agent is housed within at least one compartment within the container.

18. The device of claim 17, wherein the dose of agent is housed within a single center compartment within the container.

19. The device of claim 17 or 18, wherein the at least one compartment is cylindrically shaped.

20. The device of claim 17, wherein the at least one compartment has a cross section approximately the same as the cross section of the piercing member to minimize ahy residue of the dose of agent in the container.

21. The device of claim 18, wherein the height of the at least one compartment housing the dose of agent controls the dose of agent delivered by the device.

22. The device of claim 17, wherein a plurality of compartments each for housing a dose of agent are positioned in a circle within the container.

23. The device of claim 22, further comprising a rotating mechanism for rotating the container such that each of the plurality of compartments may be lined up with the piercing member.

24. The device of claim 23, further comprising a locking mechanism for locking the container into place during rotation, whereby the locking mechanism locks the container in place each time a compartment is lined up with the piercing member.

25. The device of claim 1, wherein a dose of agent ranges from about 5 μg to about 30 mg.

26. The device of claim 1, wherein a dose of agent ranges from about 10 μg to about 20 mg.

27. The device of claim 1, wherein the dose of agent comprises finely divided particles, the finely divided particles having diameters ranging from about 1 micron to about 50 microns.

28. The device of claim 1, wherein the dose of agent comprises finely divided particles, the finely divided particles having diameters ranging from about 3 microns to about 50 microns.

29. The device of claim 1, wherein the dose of agent is one or more medicinal agent.

30. The device of claim 1, wherein the close of agent is a liquid.

31. The device of claim 5, further comprising at least one bypass pathway extending from the canister, around the dose of agent in the container and towards to second end, whereby at least a portion of the propellant travels through the at least one bypass pathway and at least a portion of the propellant travels through the container and carries the dose of agent towards the second end.

32. The device of claim 31, wherein the portion of the propellant in the bypass pathway mixes with a portion of the propellant that travels through the container, and thereby assists in delivering the dose of agent to the mouth or nose of a user.

33. The device of claim 31 or 32, further comprising swirl chamber into which the dose of agent from the container and the portion of the propellant that travels through the container are expelled, the swirl chamber being the location where the at least one bypass pathway expels the portion of the propellant traveling through the bypass pathway.

34. The device of claim 1, wherein the propellant is a chlorofluorocarbon or hydrofluoroalkane propellant.

35. The device of claim 34, wherein the propellant is selected from hydrofluoroalkane 134a and hydrofluoroalkane 227.

36. The device of claim 1, wherein the canister further houses a dose of agent in suspension or solution.

37. The device of claim 36, wherein the dose of agent is selected from flavoring agents, surfactants, water, alcohol or other solvents, and medicinal agents.

38. The device of claim 37, wherein the dose of agent is one or more medicinal agent.

39. The device of claim 6, wherein the canister includes a valve stem through which propellant is expelled, and wherein the valve stem comprises the piercing member.

40. The device of claim 1, further comprising a stop member positioned between the canister and container, whereby the canister contacts the stop member as the canister is moved downwards and is actuated thereby.

41. The device of claim 1, further comprising a fastening mechanism connecting the first end of the body member to the second end of the body member such that the first end is separable from the second end.

42. The device of claim 1, wherein the canister includes a metering valve.

43. The device of claim 5, wherein the piercing member is a blade or blade-like member.

44. The device of claim 1, wherein the canister is a disposable single-use pressurized aerosol canister.

45. A method for the delivery of at least one dose of inhalable medicinal agents, the method comprising the steps of:

(a) providing a device for delivery of a dose of the agent comprising:

a body member having at a first end an aerosol canister housing a propellant and a second end for insertion into the mouth or nose of a user, the aerosol canister being movable downwards within the body member; and a container within the body member, for holding the dose of agent, positioned between the aerosol canister and second end; and a mechanism for exposing the dose of agent in the container to the propellant, the mechanism positioned between the canister and the container;

(b) inserting the second end of the body member into the mouth or nose of the user;

(c) actuating the aerosol canister to expel propellant through the body member towards the second end, by moving the aerosol canister towards the second end, whereby as the canister is moved towards the second end, the mechanism passes through the container thereby carrying the dose of the agent towards the second end; and (d) allowing the propellant to disperse the dose of agent from the mechanism into the mouth or nose of a user.

46. A method for the delivery of at least one dose of inhalable medicinal agents by use of device for delivery of an agent, wherein the device comprises:

(a) a body member having at a first end an aerosol canister housing a propellant and a second end for insertion into the mouth or nose of a user, the aerosol canister being movable downwards within the body member;

(b) a container within the body member, for holding the dose of agent, positioned between the aerosol canister and second end; and (c) a mechanism for exposing the dose of agent in the container to the propellant, the mechanism being positioned between the canister and the container;

wherein the method comprises:

(i) inserting the second end of the body member into the mouth or nose of the user;

(ii) actuating the aerosol canister to expel propellant through the body member towards the second end, by moving the aerosol canister towards the second end, whereby as the canister is moved towards the second end, the mechanism passes through the container, thereby carrying the dose of agent towards the second end; and (d) allowing the propellant to disperse the dose of agent from the mechanism into the mouth or nose of the user.

* * * * *